United States Patent
Mokhtari et al.

(10) Patent No.: US 9,529,286 B2
(45) Date of Patent: Dec. 27, 2016

(54) ANTIOXIDANTS FOR OVERCOAT LAYERS AND METHODS FOR MAKING THE SAME

(71) Applicant: XEROX CORPORATION, Norwalk, CT (US)

(72) Inventors: Mahya Mokhtari, Etobicoke (CA); Marko D. Saban, Toronto (CA)

(73) Assignee: XEROX CORPORATION, Norwalk, CT (US)

( * ) Notice: Subject to any disclaimer, the term of this patent is extended or adjusted under 35 U.S.C. 154(b) by 405 days.

(21) Appl. No.: 14/052,471

(22) Filed: Oct. 11, 2013

(65) Prior Publication Data

US 2015/0102529 A1    Apr. 16, 2015

(51) Int. Cl.
| | | |
|---|---|---|
| G03G 5/147 | (2006.01) |
| C07C 209/84 | (2006.01) |
| B29C 39/00 | (2006.01) |
| B29C 39/14 | (2006.01) |
| B29C 39/38 | (2006.01) |
| B29K 61/00 | (2006.01) |
| B29K 105/00 | (2006.01) |
| B29L 9/00 | (2006.01) |
| B29L 31/00 | (2006.01) |

(52) U.S. Cl.
CPC ......... *G03G 5/14769* (2013.01); *B29C 39/006* (2013.01); *B29C 39/14* (2013.01); *B29C 39/38* (2013.01); *C07C 209/84* (2013.01); *B29K 2061/00* (2013.01); *B29K 2105/0044* (2013.01); *B29L 2009/00* (2013.01); *B29L 2031/767* (2013.01)

(58) Field of Classification Search
CPC .................................................. G03G 5/14769
See application file for complete search history.

(56) References Cited

U.S. PATENT DOCUMENTS

| | | |
|---|---|---|
| 3,121,006 A | 2/1964 | Middleton et al. |
| 4,286,033 A | 8/1981 | Neyhart et al. |
| 4,291,110 A | 9/1981 | Lee |
| 4,338,387 A | 7/1982 | Hewitt |
| 4,464,450 A | 8/1984 | Teuscher |
| 4,518,669 A | 5/1985 | Yashiki |
| 4,579,801 A | 4/1986 | Yashiki |
| 4,587,189 A | 5/1986 | Hor et al. |
| 4,664,995 A | 5/1987 | Horgan et al. |
| 4,775,605 A | 10/1988 | Seki et al. |

(Continued)

FOREIGN PATENT DOCUMENTS

EP    1918779 A1    5/2008

OTHER PUBLICATIONS

Durst et al., Experimental Organic Chemistry, 1987, McGraw Hill, p. 318.*

*Primary Examiner* — Larry Thrower
(74) *Attorney, Agent, or Firm* — Pillsbury Winthrop Shaw Pittman LLP

(57) ABSTRACT

Antioxidants used for overcoat layers and processes for making the same. The present process for making the antioxidant has proven to be repeatable, cheaper, faster and safer than conventional processes. In particular, the present process uses a different solvent system where crude bis(4-diethylamino-2-methylphenyl)-(4-diethylaminophenyl-methane) is dissolved in methylethyl ketone at room temperature, followed by product precipitation in a warm mixture of ethanol and water.

20 Claims, 9 Drawing Sheets

(56) References Cited

U.S. PATENT DOCUMENTS

| | | | |
|---|---|---|---|
| 4,921,773 | A | 5/1990 | Melnyk et al. |
| 5,017,449 | A | 5/1991 | Yoshihara |
| 5,069,993 | A | 12/1991 | Robinette et al. |
| 5,153,094 | A | 10/1992 | Kazmaier et al. |
| 5,166,339 | A | 11/1992 | Duff et al. |
| 5,189,155 | A | 2/1993 | Mayo et al. |
| 5,189,156 | A | 2/1993 | Mayo et al. |
| 5,215,839 | A | 6/1993 | Yu |
| 5,344,734 | A | 9/1994 | Monbaliu et al. |
| 5,489,496 | A | 2/1996 | Katayama et al. |
| 5,641,599 | A | 6/1997 | Markovics et al. |
| 5,656,407 | A | 8/1997 | Kawahara |
| 5,660,961 | A | 8/1997 | Yu |
| 5,721,080 | A | 2/1998 | Terrell et al. |
| 5,756,245 | A | 5/1998 | Esteghamatian et al. |
| 5,958,638 | A | 9/1999 | Katayama et al. |
| 6,180,309 | B1 | 1/2001 | Maty et al. |
| 6,200,716 | B1 | 3/2001 | Fuller et al. |
| 6,207,334 | B1 | 3/2001 | Dinh et al. |
| 7,267,917 | B2 | 9/2007 | Tong et al. |
| 2008/0102388 | A1 | 5/2008 | Aziz et al. |
| 2008/0299474 | A1 | 12/2008 | McGuire et al. |
| 2015/0102529 | A1* | 4/2015 | Mokhtari ................ B29C 39/14 264/331.12 |

\* cited by examiner

ANTIOXIDANTS FOR OVERCOAT LAYERS AND METHODS FOR MAKING THE SAME

BACKGROUND

The presently disclosed embodiments relate generally to layers that are useful in imaging apparatus members and components, for use in electrostatographic, including digital, apparatuses. More particularly, the embodiments pertain to specific antioxidants for use in photoreceptor overcoat layers and processes for making the same. In embodiments, there is provided a purification process to make certain antioxidants that is repeatable as well as both shorter and cheaper than prior known processes.

Electrophotographic imaging members, e.g., photoreceptors, photoconductors, and the like, include a photoconductive layer formed on an electrically conductive substrate. The photoconductive layer is an insulator in the substantial absence of light so that electric charges are retained on its surface. Upon exposure to light, charge is generated by the photoactive pigment, and under applied field charge moves through the photoreceptor and the charge is dissipated.

In electrophotography, also known as xerography, electrophotographic imaging or electrostatographic imaging, the surface of an electrophotographic plate, drum, belt or the like (imaging member or photoreceptor) containing a photoconductive insulating layer on a conductive layer is first uniformly electrostatically charged. The imaging member is then exposed to a pattern of activating electromagnetic radiation, such as light. Charge generated by the photoactive pigment moves under the force of the applied field. The movement of the charge through the photoreceptor selectively dissipates the charge on the illuminated areas of the photoconductive insulating layer while leaving behind an electrostatic latent image. This electrostatic latent image may then be developed to form a visible image by depositing oppositely charged particles on the surface of the photoconductive insulating layer. The resulting visible image may then be transferred from the imaging member directly or indirectly (such as by a transfer or other member) to a print substrate, such as transparency or paper. The imaging process may be repeated many times with reusable imaging members.

Multilayered photoreceptors or imaging members have at least two layers, and may include a substrate, a conductive layer, an optional undercoat layer (sometimes referred to as a "charge blocking layer" or "hole blocking layer"), an optional adhesive layer, a photogenerating layer (sometimes referred to as a "charge generation layer," "charge generating layer," or "charge generator layer"), a charge transport layer, and an optional overcoating layer in either a flexible belt form or a rigid drum configuration. In the multilayer configuration, the active layers of the photoreceptor are the charge generation layer (CGL) and the charge transport layer (CTL). Enhancement of charge transport across these layers provides better photoreceptor performance. Multilayered flexible photoreceptor members may include an anti-curl layer on the backside of the substrate, opposite to the side of the electrically active layers, to render the desired photoreceptor flatness.

The charging of the photoreceptor is necessary for the proper operation of an electrostatographic apparatus. However, in normal operations of the photoreceptor, by-products are formed which can interact with the surrounding atmosphere and with the photoreceptor itself to produce substantial negative effects on the photoreceptor and the resulting copy. For example, exposure to corona effluents during xerographic cycling induces unwanted surface conductivity on the photoreceptor. The increase in surface conductivity manifests itself as a reduction in print quality. These are sometimes called lateral charge migration (LCM) and/or deletion. This effect can cause the output of a printed copy to appear blurry or have areas where the image is entirely missing (e.g., deleted). Such line spreading and/or washout occur as charges become mobile on the surface of the photoreceptor. If extended exposure occurs the washout can become severe enough to completely delete the affected print area. To suppress LCM, specific antioxidants can be incorporated into the outer photoreceptor layers. Thus, improved antioxidants and processes for making the same are always desirable.

Conventional photoreceptors are disclosed in the following patents, a number of which describe the presence of light scattering particles in the undercoat layers: Yu, U.S. Pat. No. 5,660,961; Yu, U.S. Pat. No. 5,215,839; and Katayama et al., U.S. Pat. No. 5,958,638. The term "photoreceptor" or "photoconductor" is generally used interchangeably with the terms "imaging member." The term "electrostatographic" includes "electrophotographic" and "xerographic." The terms "charge transport molecule" are generally used interchangeably with the terms "hole transport molecule."

Additional conventional photoreceptors and their materials are disclosed in, for example, U.S. Pat. Nos. 5,489,496, 4,579,801, 4,518,669, 4,775,605, 5,656,407, 5,641,599, 5,344,734, 5,721,080, 5,017,449, 6,200,716, 6,180,309, and 6,207,334, the disclosures of each of which are totally incorporated herein by reference. U.S. Pat. No. 7,267,917 (Tong et al.), the disclosure of which is totally incorporated herein by reference, discloses a charge transport layer composition for a photoreceptor including at least a binder, at least one arylamine charge transport material, e.g., N,N'-diphenyl-N,N'-bis(3-methylphenyl)-(1,1'-biphenyl)-4,4'-diamine, and at least one polymer containing carboxylic acid groups or groups capable of forming carboxylic acid groups. The charge transport layer forms a layer of photoreceptor, which also includes an optional anti-curl layer, a substrate, an optional hole blocking layer, an optional adhesive layer, a charge generating layer, and optionally one or more overcoat or protective layers.

As used herein, "discharge rate" refers to the voltage drop over time and is based upon a discharge over a discharge interval at a given light intensity, wherein discharge is defined as the voltage drop or difference between the initial surface voltage before light exposure and the surface voltage after light exposure at the end of the discharge interval. Discharge interval is defined as the time period from the light exposure stage to the development stage (which is essentially the time available for the photoreceptor surface to discharge from an initial voltage to a development voltage) and light intensity is defined as the intensity of light used to generate discharge in the photoreceptor. The exposure light intensity influences the amount of discharge, and increasing or decreasing light intensity will respectively increase or decrease the voltage drop over a given discharge interval.

SUMMARY

According to aspects illustrated herein, there is a process for making purified bis(4-diethylamino-2-methylphenyl)-(4-diethylaminophenylmethane) comprising: dissolving crude bis(4-diethylamino-2-methylphenyl)-(4-diethylaminophenylmethane) in a first solvent to form dissolved crude bis(4-diethylamino-2-methylphenyl)-(4-diethylaminophenylmethane); heating a mixture of a second solvent and a third solvent to a temperature of about 50° C. or higher to form a warm co-solvent mixture; adding the dissolved crude bis(4-diethylamino-2-methylphenyl)-(4-diethylaminophenylmethane) to the warm co-solvent mixture in a drop-wise manner to form a precipitate mixture; mixing the precipitate mixture; cooling the precipitate mixture; and drying the precipitate mixture to obtain the dried product comprising purified bis(4-diethylamino-2-methylphenyl)-(4-diethylaminophenylmethane).

Another embodiment provides a process for making purified bis(4-diethylamino-2-methylphenyl)-(4-diethylaminophenylmethane) comprising: dissolving crude bis(4-diethylamino-2-methylphenyl)-(4-diethylaminophenylmethane) in a first solvent to form dissolved crude bis(4-diethylamino-2-methylphenyl)-(4-diethylaminophenylmethane); heating a mixture of a second solvent and a third solvent to a temperature of from about 50° to about 65° C. to form a warm co-solvent mixture; adding the dissolved crude bis(4-diethylamino-2-methylphenyl)-(4-diethylaminophenylmethane) to the warm co-solvent mixture in a drop-wise manner to form a precipitate mixture; mixing the precipitate mixture; cooling the precipitate mixture; and drying the precipitate mixture to obtain the dried product comprising purified bis(4-diethylamino-2-methylphenyl)-(4-diethylaminophenylmethane), wherein the purified bis(4-diethylamino-2-methylphenyl)-(4-diethylaminophenylmethane) is of Type A polymorph.

Yet another embodiment, there is a process for making an overcoat layer for an imaging member comprising: mixing together a melamine-formaldehyde crosslinking agent, a binder, a low surface energy compound, and an acid catalyst in a solvent to form an overcoat layer solution; adding an antioxidant comprising purified bis(4-diethylamino-2-methylphenyl)-(4-diethylaminophenylmethane) to the overcoat layer solution, the process of making the antioxidant comprising dissolving crude bis(4-diethylamino-2-methylphenyl)-(4-diethylaminophenylmethane) in a first solvent to form dissolved crude bis(4-diethylamino-2-methylphenyl)-(4-diethylaminophenylmethane), heating a mixture of a second solvent and a third solvent to a temperature of from about 50° to about 65° C. to form a warm co-solvent mixture, adding the dissolved crude bis(4-diethylamino-2-methylphenyl)-(4-diethylaminophenylmethane) to the warm co-solvent mixture in a drop-wise manner to form a precipitate mixture, mixing the precipitate mixture, cooling the precipitate mixture, and drying the precipitate mixture to obtain the dried product comprising purified bis(4-diethylamino-2-methylphenyl)-(4-diethylaminophenylmethane); and drying the overcoat layer solution to yield an overcoat layer.

BRIEF DESCRIPTION OF THE DRAWINGS

For a better understanding, reference may be made to the accompanying figures.

DETAILED DESCRIPTION

Figure 1:
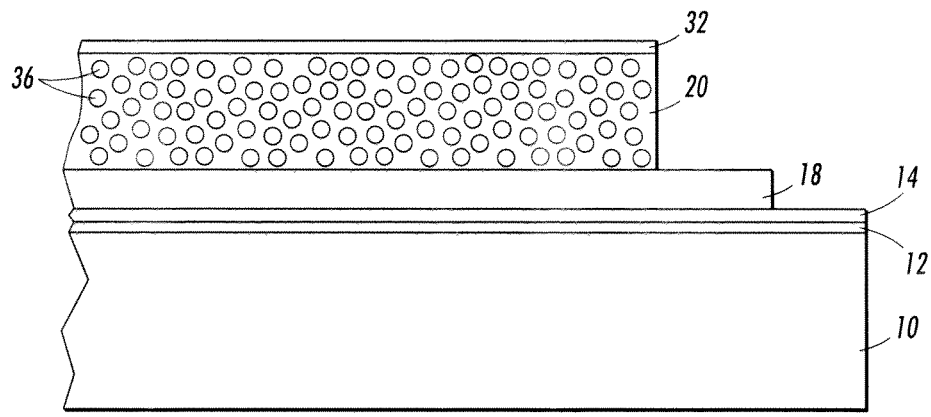
FIG. 1 is a cross-sectional view of an imaging member in a drum configuration according to the present embodiments.

In the following description, reference is made to the accompanying drawings, which form a part hereof and which illustrate several embodiments. It is understood that other embodiments may be used and structural and operational changes may be made without departure from the scope of the present disclosure.

In embodiments, there is provided a purification process to make bis(4-diethylamino-2-methylphenyl)-(4-diethylaminophenylmethane) that is repeatable as well as both shorter and cheaper than prior known processes. Briefly, the crude bis(4-diethylamino-2-methylphenyl)-(4-diethylaminophenylmethane) is dissolved in methylethyl ketone (MEK) and then precipitated into warm ethanol water. An off-white precipitate is formed. After cooling the precipitate, it is isolated and dried. The process of the present embodiments consistently produces Type A polymorph whereas the conventional process could produce either Type A or Type B. The process of the present embodiments has been found to be repeatable, giving the same high purity results each time. In addition, the process of the present embodiments is cheaper than prior conventional process because it avoids the need for maintaining a hot solvent. Lastly, the present embodiments provide a "green" and environmentally friendly process as the process does not require hot filtration of isopropanol (IPA). Thus, the present embodiments present a cheaper, reproducible and faster process that is safer to implement as compared to the previous processes. requiring hot filtration of isopropanol (IPA).

Crude bis(4-diethylamino-2-methylphenyl)-(4-diethylaminophenylmethane) was previously purified by re-crystallization in IPA and methanol mixture. Because bis(4-diethylamino-2-methylphenyl)-(4-diethylaminophenylmethane) is not soluble in IPA, high temperatures were needed to force dissolution. Thus, the conventional process involves dissolution in hot IPA, followed by hot filtration, methanol addition and cooling to room temperature. The dissolution in IPA is not repeatable. Moreover, the dissolution in IPA requires heat and is a slow step—taking over 1 hour. In addition, hot filtration is not very practical for large scale applications. Because the purified material would precipitate out of solution as soon as temperature drops below 60° C. in IPA, all of the equipment and transfer lines used would need to be heated. This is not practical at a large scale. Also, hot IPA raises other issues concerning safety and cost. For example, IPA is known to be flammable (Fp=12° C.) and heat-tracing of transfer lines at scale could be very costly. Finally, upon addition of methanol, the product would start to re-crystallize. However, the crystallization form is not predictable and the product is mostly an undesirable mixture of beads and powder. Formation of beads causes discharging problems by plugging the reactor bottom valve, and it also creates inconsistent product purity, polymorph and other quality control (QC) problems. The conventional solvent system was fraught with problems and not an ideal system.

As stated above, the present embodiments provide a process that is short, repeatable, cheaper and scale-able. This new process uses a different solvent system where crude bis(4-diethylamino-2-methylphenyl)-(4-diethylaminophenylmethane) is dissolved in methylethyl ketone at room temperature, followed by product precipitation in a warm mixture of ethanol and water.

The exemplary embodiments of this disclosure are described below with reference to the drawings. The specific terms are used in the following description for clarity, selected for illustration in the drawings and not to define or limit the scope of the disclosure. The same reference numerals are used to identify the same structure in different figures unless specified otherwise. The structures in the figures are not drawn according to their relative proportions and the drawings should not be interpreted as limiting the disclosure in size, relative size, or location. In addition, though the discussion will address negatively charged systems, the imaging members of the present disclosure may also be used in positively charged systems.

FIG. 1 is an exemplary embodiment of a multilayered electrophotographic imaging member having a drum configuration. As can be seen, the exemplary imaging member includes a rigid support substrate 10, an undercoat layer 14, a charge generation layer 18 and a charge transport layer 20. The rigid substrate may be comprised of a material selected from the group consisting of a metal, metal alloy, aluminum, zirconium, niobium, tantalum, vanadium, hafnium, titanium, nickel, stainless steel, chromium, tungsten, molybdenum, and mixtures thereof. The charge generation layer 18 and the charge transport layer 20 forms an imaging layer described here as two separate layers. In an alternative to what is shown in the figure, the charge generation layer may also be disposed on top of the charge transport layer. It will be appreciated that the functional components of these layers may alternatively be combined into a single layer.

The Overcoat Layer

Other layers of the imaging member may include, for example, an optional over coat layer 32. An optional overcoat layer 32, if desired, may be disposed over the charge transport layer 20 to provide imaging member surface protection as well as improve resistance to abrasion. In embodiments, the overcoat layer 32 may have a thickness ranging from about 0.1 micrometer to about 10 micrometers or from about 1 micrometer to about 10 micrometers, or in a specific embodiment, about 3 micrometers. These overcoating layers may include thermoplastic organic polymers or inorganic polymers that are electrically insulating or slightly semi-conductive. For example, overcoat layers may be fabricated from a dispersion including a particulate additive in a resin. Suitable particulate additives for overcoat layers include metal oxides including aluminum oxide, non-metal oxides including silica or low surface energy polytetrafluoroethylene (PTFE), and combinations thereof. Suitable resins include those described above as suitable for photogenerating layers and/or charge transport layers, for example, polyvinyl acetates, polyvinylbutyrals, polyvinylchlorides, vinylchloride and vinyl acetate copolymers, carboxyl-modified vinyl chloride/vinyl acetate copolymers, hydroxyl-modified vinyl chloride/vinyl acetate copolymers, carboxyl- and hydroxyl-modified vinyl chloride/vinyl acetate copolymers, polyvinyl alcohols, polycarbonates, polyesters, polyurethanes, polystyrenes, polybutadienes, polysulfones, polyarylethers, polyarylsulfones, polyethersulfones, polyethylenes, polypropylenes, polymethylpentenes, polyphenylene sulfides, polysiloxanes, polyacrylates, polyvinyl acetals, polyamides, polyimides, amino resins, phenylene oxide resins, terephthalic acid resins, phenoxy resins, epoxy resins, phenolic resins, polystyrene and acrylonitrile copolymers, poly-N-vinylpyrrolidinones, acrylate copolymers, alkyd resins, cellulosic film formers, poly(amideimide), styrene-butadiene copolymers, vinylidenechloride-vinylchloride copolymers, vinylacetate-vinylidenechloride copolymers, styrene-alkyd resins, polyvinylcarbazoles, and combinations thereof.

Overcoating layers may be continuous and have a thickness of at least about 0.5 micrometer, or no more than 10 micrometers, and in further embodiments have a thickness of at least about 2 micrometers, or no more than 6 micrometers.

The present overcoat layers may contain one or more antioxidants. Incorporation of antioxidants into the overcoat layer help suppress LCM. In embodiments, the antioxidant is present in the overcoat layer in an amount of from about 0.25 to about 10, or of from about 0.5 to about 3.0 by weight percent out of the total weight of the overcoat layer.

The antioxidants of the present disclosure are created by a novel process which provides several advantages over the conventionally used process. Bis(4-diethylamino-2-methylphenyl)-(4-Diethylaminophenyl-methane) (bis(4-diethylamino-2-methylphenyl)-(4-diethylaminophenylmethane)), is an antioxidant useful for the overcoat layer in next generation high speed printing machines. bis(4-diethylamino-2-methylphenyl)-(4-diethylaminophenylmethane) is prepared using a two-step procedure: 1) crude synthesis and 2) crude purification. Conventional processes of making bis(4-diethylamino-2-methylphenyl)-(4-diethylaminophenylmethane) relied upon the use of hot IPA and hot filtration. For example, the conventional process involved the following: in a jacketed reactor, IPA is heated to 70° C. Crude bis(4-diethylamino-2-methylphenyl)-(4-diethylaminophenylmethane) is added to the reactor and is mixed until it is fully dissolved (about greater than 1 hour). After the crude is dissolved, the solution is filtered hot through a 1.5μ glass fiber filter paper. The hot filtered solution is returned to the reactor and kept warm by setting the jacket to 65° C. Once the reactor temperature reaches around 65° C., methanol is added to the reactor (maintaining reactor temperature above 55° C.). After methanol addition is done, the reactor is cooled to room temperature for over 2.5 hrs. The resulting product is filtered and washed with methanol (3 times) at room temperature. The dried product is a mixture of off-white beads and powder. As discussed above, this conventional process is not repeatable and involves cost and safety concerns.

To resolve the problems associated with the conventional process of making bis(4-diethylamino-2-methylphenyl)-(4-diethylaminophenylmethane), the present embodiments provide a novel purification process which uses a different solvent system. In the present embodiments, crude bis(4-diethylamino-2-methylphenyl)-(4-diethylaminophenylmethane) is dissolved readily in methylethyl ketone (MEK) and other ketones at ambient temperature (e.g., from about 17° to about 28° C.) for about less than 10 minutes, or from about 5 to about 10 minutes so no additional energy is needed. In embodiments, the solvent used is a ketone, such as for example, one selected from the group consisting of methylethyl ketone, acetone, pentanone, cyclohexanone, and the like and mixtures thereof. The starting amount of crude bis(4-diethylamino-2-methylphenyl)-(4-diethylaminophenylmethane) and solvent can be in any amount depending on the desired amount of resulting product. In embodiments, the mass ratio of MEK to crude bis(4-diethylamino-2-methylphenyl)-(4-diethylaminophenylmethane) may be from about 1.4:1 to 1:1.

In a jacketed reactor, a mixture of ethanol and water is pre-heated to approximately 50° C. or higher, or from about 50° to about 79° C., or from about 60° to about 65° C. Any solvent in which bis(4-diethylamino-2-methylphenyl)-(4-diethylaminophenylmethane) has limited solubility can be used to mix with water to precipitate the product. In embodiments, such a solvent includes alcohols such as ethanol, methanol, isopropanol, butanol, pentanol, hexadecane-1-ol and the like and mixtures thereof. The alcohol may also include polyhydric alcohols, aliphatic alcohols and alicycle alcohols. Although any combination of the solvent and water can be used to precipitate the product, in particular embodiments, a mass ratio of ethanol to water of from about 5:95 to about 95:5 is used. In a specific embodiment, the mass ratio of ethanol to water is 5.3:1.

Once the co-solvent mixture is warm (e.g., 50° C.), the dissolved crude bis(4-diethylamino-2-methylphenyl)-(4-diethylaminophenylmethane) in MEK or other solvent is added to the reactor in a fast drop-wise manner to precipitate the product. For example, the dissolved crude bis(4-diethylamino-2-methylphenyl)-(4-diethylaminophenylmethane) is added to the warm co-solvent mixture is done at a rate starting at about 5.0 g/min. In embodiments, the rate used is from about 5.0 g/min to about 130 g/min. The rate of addition is scale-dependent. For example, the rate of 5.9 g/min was used for a 2 L bench-scale. The rate of 130 g/min was used for a 5 gal pilot scale. In both examples, to ensure consistency, the rate was calculated such that the addition time is around 30-40 minutes. However, faster rates can be used for even larger scale on a commercial level.

This is mixture is mixed for 10 minutes at 50° C. or higher, and discharged at that temperature from the reactor. A temperature of 50° C. or higher is needed because anything below this temperature will lead to agglomeration of particles during mixing. In further embodiments, the mixture may be mixed at from about 10 minutes to about 1 hour at a temperature of 50° C. to the boiling point of solvents used, or from about 50° C. to about 55° C. The mixture is then allowed to cool down to room temperature overnight prior to vacuum filtration, where the solvents and by-products are removed during the vacuum filtration. The filtration media used at the pilot scale was a 0.5 um Gortex membrane. The dried product is an off-white powder.

The process produces a product recovery yield of above 85%. In embodiments, the product recovery yield is from about 85% to about 95%. The purity of the product produced is much higher than conventional methods used. For example, the purity of the product produced by the present embodiments is above 99% as measured by high-pressure liquid chromatography (HPLC). In addition, the appearance of the product is a good indication of purity. The pure product has an appearance of white to off-white powder.

Table 1 provides a side-by-side comparison of the conventional process for making bis(4-diethylamino-2-methylphenyl)-(4-diethylaminophenylmethane) and the novel process of the present embodiments.

TABLE 1

| Process Steps | Conventional Process | Inventive Process |
|---|---|---|
| Dissolution | Unpredictable, up to several hours, Some crude lots showed less solubility in hot IPA | Reproducible, several minutes, all crude lots are soluble in MEK without any heat requirement |
| Re-Crystallization/ Precipitation | Hot filtration prior to re-crystallization is not practical, re-crystallization in hot methanol raises safety concerns for further scale-up, crystal formation is not uniform: the product is a mixture of powder and aggregates | There is no safety concerns at the temperature proposed, uniform powdery product |
| Discharge | Challenging, large aggregates blocks the drain valve | No issue |
| Filtration | Fast | Fast |
| Work-up washes | 3 re-slurry washes | Not required, one rinse over the funnel is sufficient |

Aside from the process challenges, another issue with the conventional purification process is the lack of predictability in terms of quality control parameters reflecting un-robustness of the procedure. The process of the present embodiments, however, is both repeatable and provides consistent results, as further shown in the Examples below.

The Substrate

The photoreceptor support substrate 10 may be opaque or substantially transparent, and may comprise any suitable organic or inorganic material having the requisite mechanical properties. The entire substrate can comprise the same material as that in the electrically conductive surface, or the electrically conductive surface can be merely a coating on the substrate. Any suitable electrically conductive material can be employed, such as for example, metal or metal alloy. Electrically conductive materials include copper, brass, nickel, zinc, chromium, stainless steel, conductive plastics and rubbers, aluminum, semitransparent aluminum, steel, cadmium, silver, gold, zirconium, niobium, tantalum, vanadium, hafnium, titanium, nickel, niobium, stainless steel, chromium, tungsten, molybdenum, paper rendered conductive by the inclusion of a suitable material therein or through conditioning in a humid atmosphere to ensure the presence of sufficient water content to render the material conductive, indium, tin, metal oxides, including tin oxide and indium tin oxide, and the like. It could be single metallic compound or dual layers of different metals and/or oxides.

The substrate 10 can also be formulated entirely of an electrically conductive material, or it can be an insulating material including inorganic or organic polymeric materials, such as MYLAR, a commercially available biaxially oriented polyethylene terephthalate from DuPont, or polyethylene naphthalate available as KALEDEX 2000, with a ground plane layer 12 comprising a conductive titanium or titanium/zirconium coating, otherwise a layer of an organic or inorganic material having a semiconductive surface layer, such as indium tin oxide, aluminum, titanium, and the like, or exclusively be made up of a conductive material such as, aluminum, chromium, nickel, brass, other metals and the like. The thickness of the support substrate depends on numerous factors, including mechanical performance and economic considerations.

Figure 2:
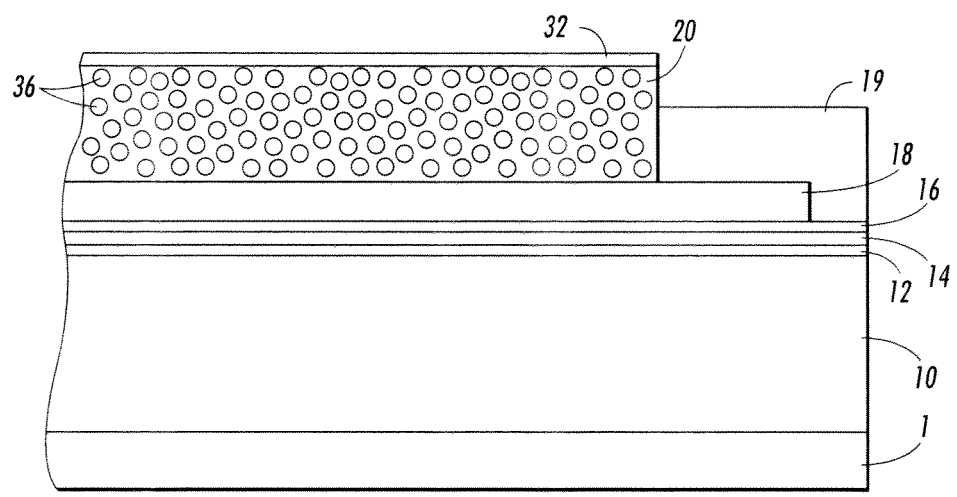
FIG. 2 is a cross-sectional view of an imaging member in a belt configuration according to the present embodiments.

The substrate 10 may have a number of many different configurations, such as for example, a plate, a cylinder, a drum, a scroll, an endless flexible belt, and the like. In the case of the substrate being in the form of a belt, as shown in FIG. 2, the belt can be seamed or seamless. In embodiments, the photoreceptor herein is in a drum configuration.

The thickness of the substrate 10 depends on numerous factors, including flexibility, mechanical performance, and economic considerations. The thickness of the support substrate 10 of the present embodiments may be at least about 500 micrometers, or no more than about 3,000 micrometers, or be at least about 750 micrometers, or no more than about 2500 micrometers.

An exemplary substrate support 10 is not soluble in any of the solvents used in each coating layer solution, is optically transparent or semi-transparent, and is thermally stable up to a high temperature of about 150° C. A substrate support 10 used for imaging member fabrication may have a thermal contraction coefficient ranging from about $1 \times 10^{-5}$ per ° C. to about $3 \times 10^{-5}$ per ° C. and a Young's Modulus of between about $5 \times 10^{-5}$ psi ($3.5 \times 10^{-4}$ Kg/cm$^2$) and about $7 \times 10^{-5}$ psi ($4.9 \times 10^{-4}$ Kg/cm$^2$).

The Ground Plane

The electrically conductive ground plane 12 may be an electrically conductive metal layer which may be formed, for example, on the substrate 10 by any suitable coating technique, such as a vacuum depositing technique. Metals include aluminum, zirconium, niobium, tantalum, vanadium, hafnium, titanium, nickel, stainless steel, chromium, tungsten, molybdenum, and other conductive substances, and mixtures thereof. The conductive layer may vary in thickness over substantially wide ranges depending on the optical transparency and flexibility desired for the electrophotoconductive member. Accordingly, for a flexible photoresponsive imaging device, the thickness of the conductive layer may be at least about 20 Angstroms, or no more than about 750 Angstroms, or at least about 50 Angstroms, or no more than about 200 Angstroms for an optimum combination of electrical conductivity, flexibility and light transmission.

Regardless of the technique employed to form the metal layer, a thin layer of metal oxide forms on the outer surface of most metals upon exposure to air. Thus, when other layers overlying the metal layer are characterized as "contiguous" layers, it is intended that these overlying contiguous layers may, in fact, contact a thin metal oxide layer that has formed on the outer surface of the oxidizable metal layer. Generally, for rear erase exposure, a conductive layer light transparency of at least about 15 percent is desirable. The conductive layer need not be limited to metals. Other examples of conductive layers may be combinations of materials such as conductive indium tin oxide as transparent layer for light having a wavelength between about 4000 Angstroms and about 9000 Angstroms or a conductive carbon black dispersed in a polymeric binder as an opaque conductive layer.

The Hole Blocking Layer

After deposition of the electrically conductive ground plane layer, the hole blocking layer 14 may be applied thereto. Electron blocking layers for positively charged photoreceptors allow holes from the imaging surface of the photoreceptor to migrate toward the conductive layer. For negatively charged photoreceptors, any suitable hole blocking layer capable of forming a barrier to prevent hole injection from the conductive layer to the opposite photoconductive layer may be utilized. The hole blocking layer may include polymers such as polyvinylbutryral, epoxy resins, polyesters, polysiloxanes, polyamides, polyurethanes and the like, or may be nitrogen containing siloxanes or nitrogen containing titanium compounds such as trimethoxysilyl propylene diamine, hydrolyzed trimethoxysilyl propyl ethylene diamine, N-beta-(aminoethyl) gamma-aminopropyl trimethoxy silane, isopropyl 4-aminobenzene sulfonyl, di(dodecylbenzene sulfonyl)titanate, isopropyl di(4-aminobenzoyl)isostearoyl titanate, isopropyl tri(N-ethylaminoethylamino)titanate, isopropyl trianthranil titanate, isopropyl tri(N,N-dimethylethylamino)titanate, titanium-4-amino benzene sulfonate oxyacetate, titanium 4-aminobenzoate isostearate oxyacetate, [H$_2$N(CH$_2$)$_4$]CH$_3$Si(OCH$_3$)$_2$, (gamma-aminobutyl)methyl diethoxysilane, and [H$_2$N(CH$_2$)$_3$]CH$_3$Si(OCH$_3$)$_2$(gamma-aminopropyl)methyl diethoxysilane, as disclosed in U.S. Pat. Nos. 4,338,387, 4,286,033 and 4,291,110.

General embodiments of the undercoat layer may comprise a metal oxide and a resin binder. The metal oxides that can be used with the embodiments herein include, but are not limited to, titanium oxide, zinc oxide, tin oxide, aluminum oxide, silicon oxide, zirconium oxide, indium oxide, molybdenum oxide, and mixtures thereof. Undercoat layer binder materials may include, for example, polyesters, MOR-ESTER 49,000 from Morton International Inc., VITEL PE-100, VITEL PE-200, VITEL PE-200D, and VITEL PE-222 from Goodyear Tire and Rubber Co., polyarylates such as ARDEL from AMOCO Production Products, polysulfone from AMOCO Production Products, polyurethanes, and the like.

The hole blocking layer should be continuous and have a thickness of less than about 0.5 micrometer because greater thicknesses may lead to undesirably high residual voltage. A hole blocking layer of between about 0.005 micrometer and about 0.3 micrometer is used because charge neutralization after the exposure step is facilitated and optimum electrical performance is achieved. A thickness of between about 0.03 micrometer and about 0.06 micrometer is used for hole blocking layers for optimum electrical behavior. The blocking layer may be applied by any suitable conventional technique such as spraying, dip coating, draw bar coating, gravure coating, silk screening, air knife coating, reverse roll coating, vacuum deposition, chemical treatment and the like. For convenience in obtaining thin layers, the blocking layer is applied in the form of a dilute solution, with the solvent being removed after deposition of the coating by conventional techniques such as by vacuum, heating and the like. Generally, a weight ratio of hole blocking layer material and solvent of between about 0.05:100 to about 0.5:100 is satisfactory for spray coating.

The Charge Generation Layer

The charge generation layer 18 may thereafter be applied to the undercoat layer 14. Any suitable charge generation binder including a charge generating/photoconductive material, which may be in the form of particles and dispersed in a film forming binder, such as an inactive resin, may be utilized. Examples of charge generating materials include, for example, inorganic photoconductive materials such as amorphous selenium, trigonal selenium, and selenium alloys selected from the group consisting of selenium-tellurium, selenium-tellurium-arsenic, selenium arsenide and mixtures thereof, and organic photoconductive materials including various phthalocyanine pigments such as the X-form of metal free phthalocyanine, metal phthalocyanines such as vanadyl phthalocyanine and copper phthalocyanine, hydroxy gallium phthalocyanines, chlorogallium phthalocyanines, titanyl phthalocyanines, quinacridones, dibromo anthanthrone pigments, benzimidazole perylene, substituted 2,4-diamino-triazines, polynuclear aromatic quinones, enzimidazole perylene, and the like, and mixtures thereof, dispersed in a film forming polymeric binder. Selenium, selenium alloy, benzimidazole perylene, and the like and mixtures thereof may be formed as a continuous, homogeneous charge generation layer. Benzimidazole perylene compositions are well known and described, for example, in U.S. Pat. No. 4,587,189, the entire disclosure thereof being incorporated herein by reference. Multi-charge generation layer compositions may be used where a photoconductive layer enhances or reduces the properties of the charge generation layer. Other suitable charge generating materials known in the art may also be utilized, if desired. The charge generating materials selected should be sensitive to activating radiation having a wavelength between about 400 and about 900 nm during the imagewise radiation exposure step in an electrophotographic imaging process to form an electrostatic latent image. For example, hydroxygallium phthalocyanine absorbs light of a wavelength of from about 370 to about 950 nanometers, as disclosed, for example, in U.S. Pat. No. 5,756,245.

A number of titanyl phthalocyanines, or oxytitanium phthalocyanines for the photoconductors illustrated herein are photogenerating pigments known to absorb near infrared light around 800 nanometers, and may exhibit improved sensitivity compared to other pigments, such as, for example, hydroxygallium phthalocyanine. Generally, titanyl phthalocyanine is known to have five main crystal forms known as Types I, II, III, X, and IV. For example, U.S. Pat. Nos. 5,189,155 and 5,189,156, the disclosures of which are totally incorporated herein by reference, disclose a number of methods for obtaining various polymorphs of titanyl phthalocyanine. Additionally, U.S. Pat. Nos. 5,189,155 and 5,189,156 are directed to processes for obtaining Types I, X, and IV phthalocyanines. U.S. Pat. No. 5,153,094, the disclosure of which is totally incorporated herein by reference, relates to the preparation of titanyl phthalocyanine polymorphs including Types I, II, III, and IV polymorphs. U.S. Pat. No. 5,166,339, the disclosure of which is totally incorporated herein by reference, discloses processes for preparing Types I, IV, and X titanyl phthalocyanine polymorphs, as well as the preparation of two polymorphs designated as Type Z-1 and Type Z-2.

Any suitable inactive resin materials may be employed as a binder in the charge generation layer 18, including those described, for example, in U.S. Pat. No. 3,121,006, the entire disclosure thereof being incorporated herein by reference. Organic resinous binders include thermoplastic and thermosetting resins such as one or more of polycarbonates, polyesters, polyamides, polyurethanes, polystyrenes, polyarylethers, polyarylsulfones, polybutadienes, polysulfones, polyethersulfones, polyethylenes, polypropylenes, polyimides, polymethylpentenes, polyphenylene sulfides, polyvinyl butyral, polyvinyl acetate, polysiloxanes, polyacrylates, polyvinyl acetals, polyamides, polyimides, amino resins, phenylene oxide resins, terephthalic acid resins, epoxy resins, phenolic resins, polystyrene and acrylonitrile copolymers, polyvinylchloride, vinylchloride and vinyl acetate copolymers, acrylate copolymers, alkyd resins, cellulosic film formers, poly(amideimide), styrene-butadiene copolymers, vinylidenechloride/vinylchloride copolymers, vinylacetate/vinylidene chloride copolymers, styrene-alkyd resins, and the like. Another film-forming polymer binder is PCZ-400 (poly(4,4'-dihydroxy-diphenyl-1-1-cyclohexane) which has a viscosity-molecular weight of 40,000 and is available from Mitsubishi Gas Chemical Corporation (Tokyo, Japan).

The charge generating material can be present in the resinous binder composition in various amounts. Generally, at least about 5 percent by volume, or no more than about 90 percent by volume of the charge generating material is dispersed in at least about 95 percent by volume, or no more than about 10 percent by volume of the resinous binder, and more specifically at least about 20 percent, or no more than about 60 percent by volume of the charge generating material is dispersed in at least about 80 percent by volume, or no more than about 40 percent by volume of the resinous binder composition.

In specific embodiments, the charge generation layer 18 may have a thickness of at least about 0.1 µm, or no more than about 2 µm, or of at least about 0.2 µm, or no more than about 1 µm. These embodiments may be comprised of chlorogallium phthalocyanine or hydroxygallium phthalocyanine or mixtures thereof. The charge generation layer 18 containing the charge generating material and the resinous binder material generally ranges in thickness of at least about 0.1 µm, or no more than about 5 µm, for example, from about 0.2 µm to about 3 µm when dry. The charge generation layer thickness is generally related to binder content. Higher binder content compositions generally employ thicker layers for charge generation.

The Charge Transport Layer

In a drum photoreceptor, the charge transport layer comprises a single layer of the same composition. As such, the charge transport layer will be discussed specifically in terms of a single layer 20, but the details will be also applicable to an embodiment having dual charge transport layers. The charge transport layer 20 is thereafter applied over the charge generation layer 18 and may include any suitable transparent organic polymer or non-polymeric material capable of supporting the injection of photogenerated holes or electrons from the charge generation layer 18 and capable of allowing the transport of these holes/electrons through the charge transport layer to selectively discharge the surface charge on the imaging member surface. In one embodiment, the charge transport layer 20 not only serves to transport holes, but also protects the charge generation layer 18 from abrasion or chemical attack and may therefore extend the service life of the imaging member. The charge transport layer 20 can be a substantially non-photoconductive material, but one which supports the injection of photogenerated holes from the charge generation layer 18.

FIG. 2 shows an imaging member having a belt configuration according to the embodiments. As shown, the belt configuration is provided with an anti-curl back coating 1, a supporting substrate 10, an electrically conductive ground plane 12, an undercoat layer 14, an adhesive layer 16, a charge generation layer 18, and a charge transport layer 20. An optional overcoat layer 32 and ground strip 19 may also be included. An exemplary photoreceptor having a belt configuration is disclosed in U.S. Pat. No. 5,069,993, which is hereby incorporated by reference. In embodiments, the charge transport layer 20 comprises specific anti-oxidants 36 to provide increased LCM resistance for the imaging member and better subsequent print quality. The anti-oxidant 36 is present in an amount of from about 1% to about 30 wt % of the total weight of the charge transport layer 20. In other embodiments, the anti-oxidant 36 is present in an amount of from about 10% to about 15 wt % of the total weight of the charge transport layer. In embodiments, the charge transport layer may comprise two or more different anti-oxidants.

In specific embodiments, the anti-oxidant 36 is selected from the group consisting of 2,5-di(tert-amyl)hydroquinone, 2,2'-Methylenebis(4-ethyl-6-tert-butylphenol), and mixtures thereof. In one embodiment, the specific combination of four active components: high quality N,N,N,'N'-tetra(4-methylphenyl)-(1,1'-biphenyl)-4,4'-diamine, 2,5-di(tert-amyl)hydroquinone, 2,2'-Methylenebis(4-ethyl-6-tert-butylphenol) and an acid polymer produces a unique photoreceptor that clearly demonstrates substantial improvement in performance over conventional designs. The addition of the terpolymer helps counter the negative impact of the hydroquinone anti-oxidant on the discharge performance of the photoreceptor. In embodiments, the acid terpolymer is present in the charge transport layer in an amount of from about 1% to about 20% by weight of the total weight of the charge transport layer. In other embodiments, the N,N,N,'N'-tetra (4-methylphenyl)-(1,1'-biphenyl)-4,4'-diamine is present in the charge transport layer in an amount of from about 10% to about 60% by weight of the total weight of the charge transport layer.

In further embodiments, the charge transport layer further comprises a film forming polymer material selected from the group consisting of at least one of polycarbonates, polystyrenes, polyarylates, polyesters, polyimides, polysiloxanes, polysulfones, polyphenyl sulfides, polyetherimides, and polyphenylene vinylenes. In more specific embodiments, the polymer comprises a film forming polymer material selected from the group consisting of poly(bisphenol-A carbonate), poly(bisphenol-Z carbonate), poly(bisphenol-A carbonate)-co-poly(bisphenol-Z carbonate).

In embodiments, the acid polymer is a vinyl chloride/vinyl acetate/maleic acid terpolymer. In this embodiment, the vinyl chloride monomer is present in the polymer in any desired or effective amount, in one embodiment at least about 50 percent by weight, in another embodiment at least about 70 percent by weight, and in yet another embodiment at least about 80 percent by weight, and in one embodiment no more than about 90 percent by weight, although the amount can be outside of these ranges. The vinyl acetate monomer is present in the polymer in any desired or effective amount, in one embodiment at least about 5 percent by weight, and in another embodiment at least about 10 percent by weight, and in one embodiment no more than about 25 percent by weight, in another embodiment no more than about 20 percent by weight, and in yet another embodiment no more than about 15 percent by weight, although the amount can be outside of these ranges. The maleic acid monomer is present in the polymer in any desired or effective amount, in one embodiment at least about 0.2 percent by weight, and in another embodiment at least about 0.5 percent by weight, and in one embodiment no more than about 5 percent by weight, in another embodiment no more than about 2 percent by weight, and in yet another embodiment no more than about 1.5 percent by weight, although the amount can be outside of these ranges.

Examples of suitable acid polymers include VMCH, available from Dow Chemical Co., Midland, Mich., having about 86 percent by weight vinyl chloride, about 13 percent by weight vinyl acetate, and about 1 percent by weight maleic acid, and a number average molecular weight of about 27,000, UCAR® VMCH, available from Union Carbide Corporation, Danbury, Conn., having about 86 percent by weight vinyl chloride, about 13 percent by weight vinyl acetate, and about 1 percent by weight maleic acid, UCAR® VMCC, available from Union Carbide Corporation, having about 86 percent by weight vinyl chloride, about 13 percent by weight vinyl acetate, and about 1 percent by weight maleic acid, UCAR® VMCA, available from Union Carbide Corporation, having about 81 percent by weight vinyl chloride, about 17 percent by weight vinyl acetate, and about 2 percent by weight maleic acid, and the like, as well as mixtures thereof.

Other optional anti-oxidants that can be incorporated into the charge transport layers or at least one charge transport layer to enable improved LCM resistance include hindered phenolic anti-oxidants such as tetrakis methylene(3,5-di-tert-butyl-4-hydroxy hydrocinnamate) methane (IRGANOX® 1010, available from Ciba Specialty Chemical), butylated hydroxytoluene (BHT), and other hindered phenolic anti-oxidants including SUMILIZER™ BHT-R, MDP-S, BBM-S, WX-R, NR, BP-76, BP-101, GA-80, GM and GS (available from Sumitomo Chemical Co., Ltd.), IRGANOX® 1035, 1076, 1098, 1135, 1141, 1222, 1330, 1425WL, 1520L, 245, 259, 3114, 3790, 5057 and 565 (available from Ciba Specialties Chemicals), and ADEKA STAB™ AO-20. AO-30, AO-40, AO-50, AO-60, AO-70, AO-80 and AO-330 (available from Asahi Denka Co., Ltd.); hindered amine anti-oxidants such as SANOL™ LS-2626, LS-765, LS-770 and LS-744 (available from SANKYO CO., Ltd.), TINUVIN® 144 and 622LD (available from Ciba Specialties Chemicals), MARK™ LA57, LA67, LA62, LA68 and LA63 (available from Asahi Denka Co., Ltd.), and SUMILIZER® TPS (available from Sumitomo Chemical Co., Ltd.); thioether anti-oxidants such as SUMILIZER® TP-D (available from Sumitomo Chemical Co., Ltd); phosphite anti-oxidants such as MARK™ 2112, PEP-8, PEP-24G, PEP-36, 329K and HP-10 (available from Asahi Denka Co., Ltd.); other molecules such as bis(4-diethylamino-2-methylphenyl) phenylmethane (BDETPM), bis-[2-methyl-4-(N-2-hydroxyethyl-N-ethyl-aminophenyl)]-phenylmethane (DHTPM), and the like. The weight percent of the anti-oxidant in at least one of the charge transport layer is from about 0 to about 20, from about 1 to about 10, or from about 3 to about 8 weight percent.

The layer 20 is normally transparent in a wavelength region in which the electrophotographic imaging member is to be used when exposure is affected there to ensure that most of the incident radiation is utilized by the underlying charge generation layer 18. The charge transport layer should exhibit excellent optical transparency with negligible light absorption and no charge generation when exposed to a wavelength of light useful in xerography, e.g., 400 to 900 nanometers. In the case when the photoreceptor is prepared with the use of a transparent substrate 10 and also a transparent or partially transparent conductive layer 12, image wise exposure or erase may be accomplished through the substrate 10 with all light passing through the back side of the substrate. In this case, the materials of the layer 20 need not transmit light in the wavelength region of use if the charge generation layer 18 is sandwiched between the substrate and the charge transport layer 20. The charge transport layer 20 in conjunction with the charge generation layer 18 is an insulator to the extent that an electrostatic charge placed on the charge transport layer is not conducted in the absence of illumination. The charge transport layer 20 should trap minimal charges as the charge passes through it during the discharging process.

The charge transport layer 20 may include any suitable charge transport component or activating compound useful as an additive dissolved or molecularly dispersed in an electrically inactive polymeric material, such as a polycarbonate binder, to form a solid solution and thereby making this material electrically active. "Dissolved" refers, for example, to forming a solution in which the small molecule is dissolved in the polymer to form a homogeneous phase; and molecularly dispersed in embodiments refers, for example, to charge transporting molecules dispersed in the polymer, the small molecules being dispersed in the polymer on a molecular scale. The charge transport component may be added to a film forming polymeric material which is otherwise incapable of supporting the injection of photogenerated holes from the charge generation material and incapable of allowing the transport of these holes through. This addition converts the electrically inactive polymeric material to a material capable of supporting the injection of photogenerated holes from the charge generation layer 18 and capable of allowing the transport of these holes through the charge transport layer 20 in order to discharge the surface charge on the charge transport layer. The high mobility charge transport component may comprise small molecules of an organic compound which cooperate to transport charge between molecules and ultimately to the surface of the charge transport layer.

The charge transport material is present in the charge transport layer in any desired or effective amount, in one embodiment at least about 5 percent by weight, in another embodiment at least about 20 percent by weight, and in yet another embodiment at least about 30 percent by weight, and in one embodiment no more than about 90 percent by weight, in another embodiment no more than about 75 percent by weight, and in another embodiment no more than about 60 percent by weight, although the amount can be outside of these ranges.

One specific suitable charge transport material is high quality N,N,N'N'-tetra(4-methylphenyl)-(1,1'-biphenyl)-4,4'-diamine, of the formula

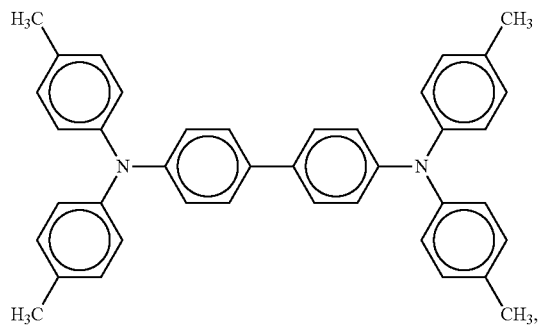

as disclosed in, for example, U.S. Patent Publication 20080102388, U.S. Patent Publication 20080299474, filed May 31, 2007, and European Patent Publication EP 1 918 779 A1, the disclosures of each of which are totally incorporated herein by reference.

As used herein, "high quality" referring to the substituted biphenyl diamine thus refers to a substituted biphenyl diamine that, when incorporated into a photoreceptor, the photoreceptor will discharge from about 90% to about 100% of its surface potential in from 0 to about 40 milliseconds upon being subjected to xerographic charging and exposure to radiant energy of about 1 ergs/cm$^2$ to about 3 ergs/cm$^2$. In embodiments, a photoreceptor comprising the high quality substituted biphenyl diamine may have a post erase voltage of from about 0 to about 10 volts, from an initial charging voltage of from about 400 to about 1000 volts, when erase energy is about 200 ergs/cm$^2$. The substituted biphenyl diamine may also exhibit stable xerographic cycling over 10,000 cycles.

In addition to a high quality substituted biphenyl diamine, the present disclosure in embodiments is directed to a substituted biphenyl diamine of high purity, such as for example, a purity of from about 95 percent to about 100 percent, such as from about 98 percent to about 100 percent, as determined for example, by HPLC, NMR, GC, LC/MS. GC/MS or by melting temperature data.

Although not limited to any specific theory, it is believed that the high quality of the substituted biphenyl diamine, and the properties provided thereby, may not be directly linked to its chemical purity alone, but instead may be linked to the chemical purity, type and amount of residual impurities, and the like.

A number of charge transport compounds can be included in the charge transport layer, which layer generally is of a thickness of from about 5 to about 75 micrometers, and more specifically, of a thickness of from about 15 to about 40 micrometers. Examples of charge transport components are aryl amines of the following formulas/structures:

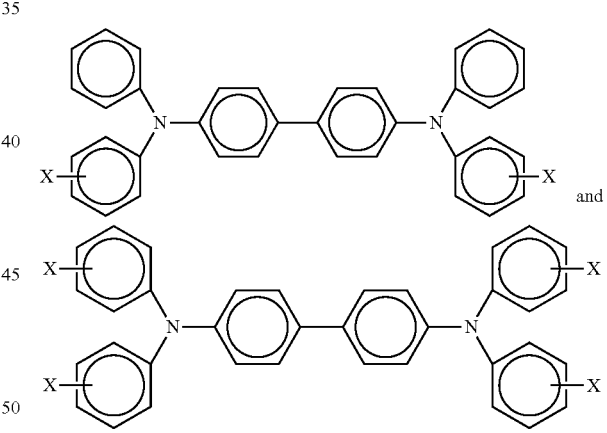
and wherein X is a suitable hydrocarbon like alkyl, alkoxy, aryl, and derivatives thereof; a halogen, or mixtures thereof, and especially those substituents selected from the group consisting of Cl and CH$_3$; and molecules of the following formulas

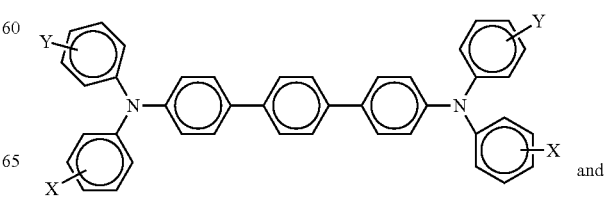
and

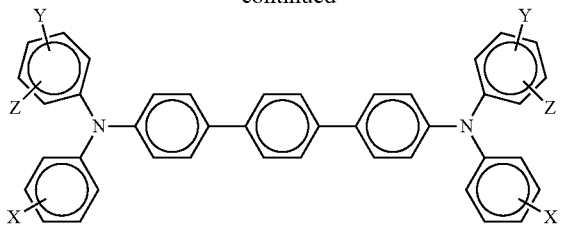

wherein X, Y and Z are independently alkyl, alkoxy, aryl, a halogen, or mixtures thereof, and wherein at least one of Y and Z are present.

Alkyl and alkoxy contain, for example, from 1 to about 25 carbon atoms, and more specifically, from 1 to about 12 carbon atoms, such as methyl, ethyl, propyl, butyl, pentyl, and the corresponding alkoxides. Aryl can contain from 6 to about 36 carbon atoms, such as phenyl, and the like. Halogen includes chloride, bromide, iodide, and fluoride. Substituted alkyls, alkoxys, and aryls can also be selected in embodiments.

Examples of specific aryl amines that can be selected for the charge transport layer include N,N'-diphenyl-N,N'-bis(alkylphenyl)-1,1-biphenyl-4,4'-diamine wherein alkyl is selected from the group consisting of methyl, ethyl, propyl, butyl, hexyl, and the like; N,N'-diphenyl-N,N'-bis(halophenyl)-1,1'-biphenyl-4,4'-diamine wherein the halo substituent is a chloro substituent; N,N'-bis(4-butylphenyl)-N,N'-di-p-tolyl-[p-terphenyl]-4,4"-diamine, N,N'-bis(4-butylphenyl)-N,N'-di-m-tolyl-[p-terphenyl]-4,4"-diamine, N,N'-bis(4-butylphenyl)-N,N'-di-o-tolyl-[p-terphenyl]-4,4"-diamine, N,N'-bis(4-butylphenyl)-N,N'-bis-(4-isopropylphenyl)-[p-terphenyl]-4,4"-diamine, N,N'-bis(4-butylphenyl)-N,N'-bis-(2-ethyl-6-methylphenyl)-[p-terphenyl]-4,4"-diamine, N,N'-bis(4-butylphenyl)-N,N'-bis-(2,5-dimethylphenyl)-[p-terphenyl]-4,4'-diamine, N,N'-diphenyl-N,N'-bis(3-chlorophenyl)-[p-terphenyl]-4,4"-diamine, and the like. Other known charge transport layer molecules may be selected in embodiments, reference for example, U.S. Pat. Nos. 4,921,773 and 4,464,450, the disclosures of which are totally incorporated herein by reference.

Examples of the highly insulating and transparent resinous components or inactive binder resinous material for the transport layers include materials such as those described in U.S. Pat. No. 3,121,006, the disclosure of which is totally incorporated herein by reference. Specific examples of suitable organic resinous materials include polycarbonates, such as MAKROLON 5705 from Farbenfabriken Bayer AG or FPC0170 from Mitsubishi Gas Chemical Co., acrylate polymers, vinyl polymers, cellulose polymers, polyesters, polysiloxanes, polyamides, polyurethanes, polystyrenes, polyarylates, polyethers, polysulfones, and epoxies, as well as block, random or alternating copolymers thereof. Specific examples include polycarbonates such as poly(4,4'-isopropylidene-diphenylene)carbonate (also referred to as bisphenol-A-polycarbonate, poly(4,4'-cyclohexylidinediphenylene)carbonate (referred to as bisphenol-Z polycarbonate), poly(4,4'-isopropylidene-3,3'-dimethyl-diphenyl)carbonate (also referred to as bisphenol-C-polycarbonate), and the like. Specific examples of electrically inactive binder materials include polycarbonate resins having a number average molecular weight of from about 20,000 to about 150,000 with a molecular weight in the range of from about 50,000 to about 100,000 being particularly preferred. Any suitable charge transporting polymer can also be used in the charge transporting layer.

The charge transport layer should be an insulator to the extent that the electrostatic charge placed on the hole transport layer is not conducted in the absence of illumination at a rate sufficient to prevent formation and retention of an electrostatic latent image thereon. The charge transport layer is substantially nonabsorbing to visible light or radiation in the region of intended use, but is electrically "active" in that it allows the injection of photogenerated holes from the photoconductive layer, that is the charge generation layer, and allows these holes to be transported through itself to selectively discharge a surface charge on the surface of the active layer.

Any suitable and conventional technique may be utilized to form and thereafter apply the charge transport layer mixture to the supporting substrate layer. The charge transport layer may be formed in a single coating step or in multiple coating steps. Dip coating, ring coating, spray, gravure or any other drum coating methods may be used.

Drying of the deposited coating may be effected by any suitable conventional technique such as oven drying, infra red radiation drying, air drying and the like. The thickness of the charge transport layer after drying is from about 10 μm to about 40 μm or from about 12 μm to about 36 μm for optimum photoelectrical and mechanical results. In another embodiment the thickness is from about 14 μm to about 36 μm.

The Adhesive Layer

An optional separate adhesive interface layer may be provided in certain configurations, such as for example, in flexible web configurations. In the embodiment illustrated in FIG. 1, the interface layer would be situated between the blocking layer 14 and the charge generation layer 18. The interface layer may include a copolyester resin. Exemplary polyester resins which may be utilized for the interface layer include polyarylatepolyvinylbutyrals, such as ARDEL POLYARYLATE (U-100) commercially available from Toyota Hsutsu Inc., VITEL PE-100, VITEL PE-200, VITEL PE-200D, and VITEL PE-222, all from Bostik, 49,000 polyester from Rohm Hass, polyvinyl butyral, and the like. The adhesive interface layer may be applied directly to the hole blocking layer 14. Thus, the adhesive interface layer in embodiments is in direct contiguous contact with both the underlying hole blocking layer 14 and the overlying charge generator layer 18 to enhance adhesion bonding to provide linkage. In yet other embodiments, the adhesive interface layer is entirely omitted.

Any suitable solvent or solvent mixtures may be employed to form a coating solution of the polyester for the adhesive interface layer. Solvents may include tetrahydrofuran, toluene, monochlorobenzene, methylene chloride, cyclohexanone, and the like, and mixtures thereof. Any other suitable and conventional technique may be used to mix and thereafter apply the adhesive layer coating mixture to the hole blocking layer. Application techniques may include spraying, dip coating, roll coating, wire wound rod coating, and the like. Drying of the deposited wet coating may be effected by any suitable conventional process, such as oven drying, infra red radiation drying, air drying, and the like.

The adhesive interface layer may have a thickness of at least about 0.01 micrometers, or no more than about 900 micrometers after drying. In embodiments, the dried thickness is from about 0.03 micrometers to about 1 micrometer.

The Ground Strip

The ground strip may comprise a film forming polymer binder and electrically conductive particles. Any suitable electrically conductive particles may be used in the electrically conductive ground strip layer 19. The ground strip 19 may comprise materials which include those enumerated in U.S. Pat. No. 4,664,995. Electrically conductive particles include carbon black, graphite, copper, silver, gold, nickel, tantalum, chromium, zirconium, vanadium, niobium, indium tin oxide and the like. The electrically conductive particles may have any suitable shape. Shapes may include irregular, granular, spherical, elliptical, cubic, flake, filament, and the like. The electrically conductive particles should have a particle size less than the thickness of the electrically conductive ground strip layer to avoid an electrically conductive ground strip layer having an excessively irregular outer surface. An average particle size of less than about 10 micrometers generally avoids excessive protrusion of the electrically conductive particles at the outer surface of the dried ground strip layer and ensures relatively uniform dispersion of the particles throughout the matrix of the dried ground strip layer. The concentration of the conductive particles to be used in the ground strip depends on factors such as the conductivity of the specific conductive particles utilized.

The ground strip layer may have a thickness of at least about 7 micrometers, or no more than about 42 micrometers, or of at least about 14 micrometers, or no more than about 27 micrometers.

The Anti-Curl Back Coating Layer

The anti-curl back coating 1 may comprise organic polymers or inorganic polymers that are electrically insulating or slightly semi-conductive. The anti-curl back coating provides flatness and/or abrasion resistance.

Anti-curl back coating 1 may be formed at the back side of the substrate 2, opposite to the imaging layers. The anti-curl back coating may comprise a film forming resin binder and an adhesion promoter additive. The resin binder may be the same resins as the resin binders of the charge transport layer discussed above. Examples of film forming resins include polyacrylate, polystyrene, bisphenol polycarbonate, poly(4,4'-isopropylidene diphenyl carbonate), 4,4'-cyclohexylidene diphenyl polycarbonate, and the like. Adhesion promoters used as additives include 49,000 (du Pont), Vitel PE-100, Vitel PE-200, Vitel PE-307 (Goodyear), and the like. Usually from about 1 to about 15 weight percent adhesion promoter is selected for film forming resin addition. The thickness of the anti-curl back coating is at least about 3 micrometers, or no more than about 35 micrometers, or about 14 micrometers.

In addition, in the present embodiments using a belt configuration, the charge transport layer may consist of a single pass charge transport layer or a dual pass charge transport layer (or dual layer charge transport layer) with the same or different transport molecule ratios. In these embodiments, the dual layer charge transport layer has a total thickness of from about 10 μm to about 40 μm. In other embodiments, each layer of the dual layer charge transport layer may have an individual thickness of from 2 μm to about 20 μm. Moreover, the charge transport layer may be configured such that it is used as a top layer of the photoreceptor to inhibit crystallization at the interface of the charge transport layer and the overcoat layer. In another embodiment, the charge transport layer may be configured such that it is used as a first pass charge transport layer to inhibit microcrystallization occurring at the interface between the first pass and second pass layers.

Various exemplary embodiments encompassed herein include a method of imaging which includes generating an electrostatic latent image on an imaging member, developing a latent image, and transferring the developed electrostatic image to a suitable substrate.

While the description above refers to particular embodiments, it will be understood that many modifications may be made without departing from the spirit thereof. The accompanying claims are intended to cover such modifications as would fall within the true scope and spirit of embodiments herein.

The presently disclosed embodiments are, therefore, to be considered in all respects as illustrative and not restrictive, the scope of embodiments being indicated by the appended claims rather than the foregoing description. All changes that come within the meaning of and range of equivalency of the claims are intended to be embraced therein.

EXAMPLES

The example set forth herein below and is illustrative of different compositions and conditions that can be used in practicing the present embodiments. All proportions are by weight unless otherwise indicated. It will be apparent, however, that the embodiments can be practiced with many types of compositions and can have many different uses in accordance with the disclosure above and as pointed out hereinafter.

Controls 1 and 2

The controls are made using the conventional process where crude bis(4-diethylamino-2-methylphenyl)-(4-diethylaminophenylmethane) is purified by re-crystallization in IPA and methanol mixture. Because bis(4-diethylamino-2-methylphenyl)-(4-diethylaminophenylmethane) is not soluble in IPA, high temperatures were needed to force dissolution. Thus, the crude solution is dissolved in hot IPA followed by a hot filtration and precipitation in methanol.

Example 1

In a 1 liter jacketed reactor, a mixture of 400 ml ethanol and 60 ml deionized water (DIW), is pre-heated to approximately 53° C. Meanwhile, 36 g of crude TRIS TPM is readily dissolved into 80 ml of MEK at room temperature. When the reactor temperature is around 53° C., the crude solution is added to the reactor over 20 minutes. After 15 minutes of additional mixing, the reactor content is discharged immediately warm into a beaker. The beaker was covered and left in the fume-hood over night for a gentle cool down to room temperature. More crystallization occurs as the mixture cools down to room temperature. The next morning, the product is filtered through a #935AH Glass fiber filter paper and is rinsed with 50 ml of methanol once. The product is placed in a vacuum oven overnight at approximately 55° C. (30.55 g, 85% theoretical yield).

The process was implemented in a scale-up experiment in a pilot plant facility and was successfully scaled-up to 5 gallon.

Example 2

A second sample was made and obtained in the same procedure as described in Example 1.

Results

A summary of important quality control parameters is provided in the following Table 2. The first two samples are the control bis(4-diethylamino-2-methylphenyl)-(4-diethylaminophenylmethane) made according to the conventional process and the latter two samples are the bis(4-diethyl amino-2-methylphenyl)-(4-diethylaminophenylmethane) made according to the novel processes of the present embodiments described herein.

TABLE 2

| Sample ID | Final dried product mass (g) | Yield (%) | Purity (by HPLC) | DSC (mp, ° C.) | XRD |
|---|---|---|---|---|---|
| Control 1 | N/A | N/A | 99.75% | 104.6 | Type B |
| Control 2 | N/A | N/A | 99.6% | 98.3 | Type A |
| Example 1 | 29.4 | 82% | 99.0% | 96.65 | Type A |
| Example 2 | 30.6 | 85% | 99.1% | 96.99 | Type A |

Figure 3A:
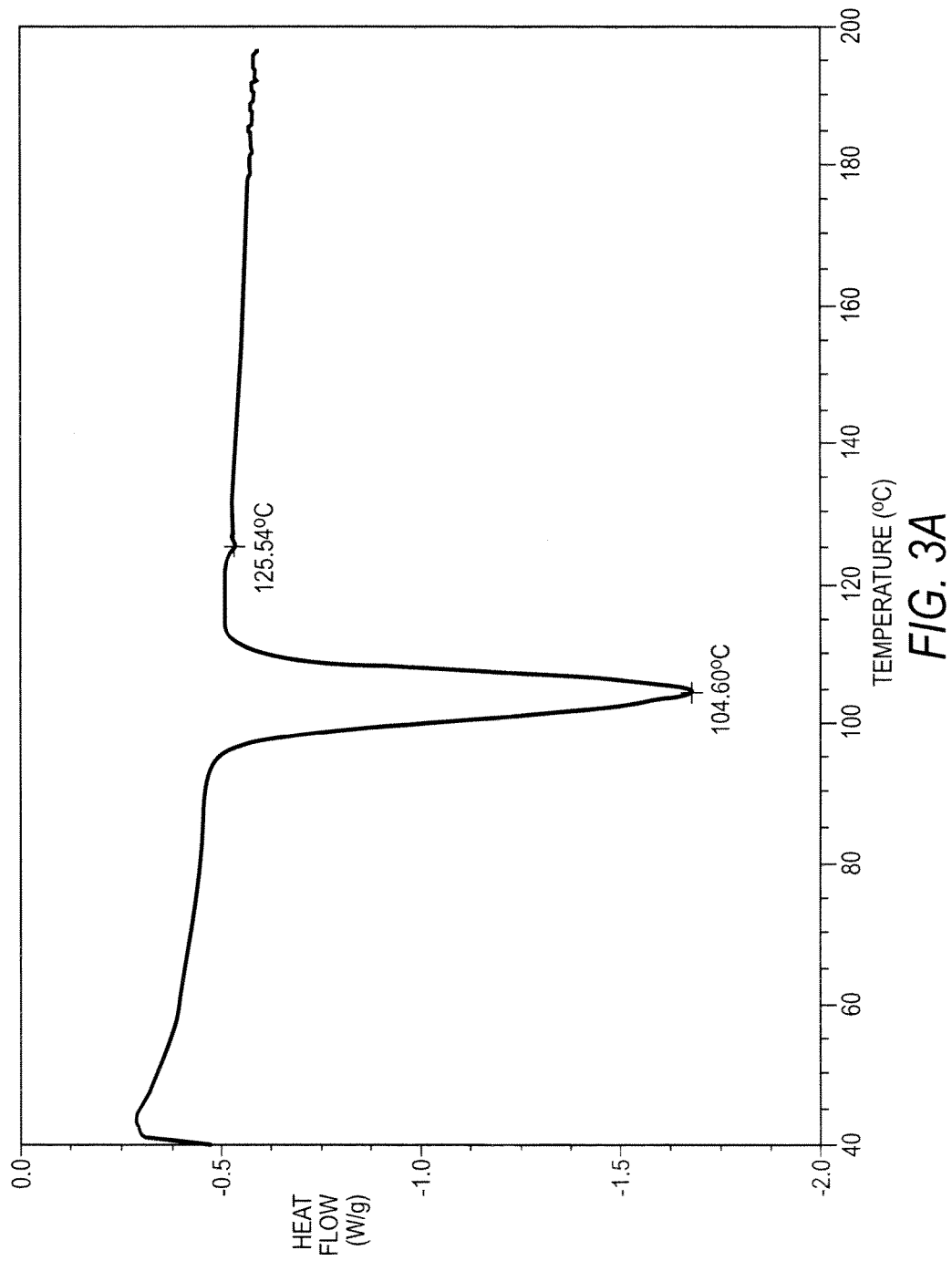
FIG. 3A is an evaluation made by differential scanning calorimetry (DSC) of the resulting product made by the conventional processes for making bis(4-diethylamino-2-methylphenyl)-(4-diethylaminophenylmethane)
Figure 3B:
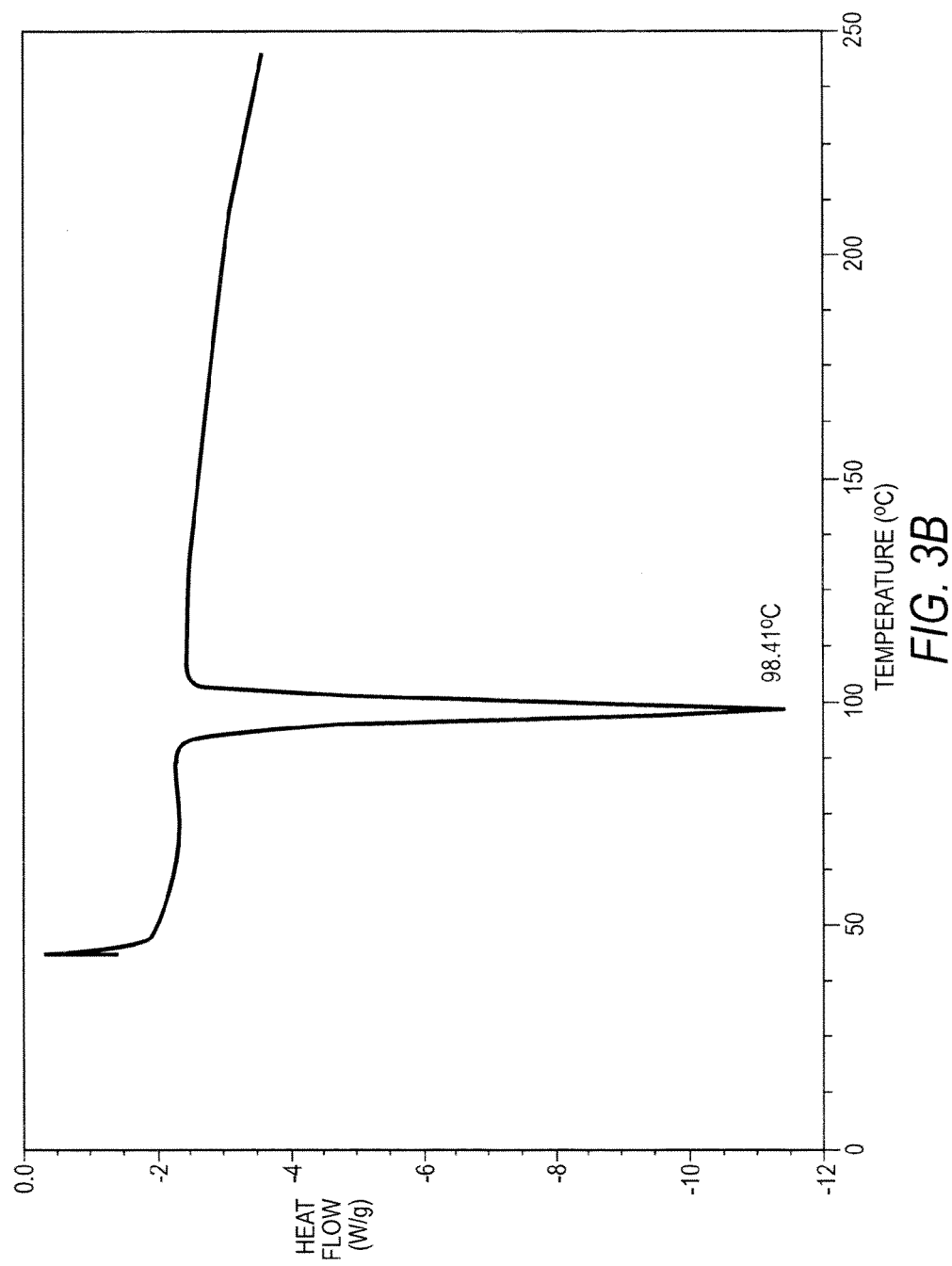
FIG. 3B is an evaluation made by differential scanning calorimetry (DSC) of another resulting product made by the conventional processes for making bis(4-diethylamino-2-methylphenyl)-(4-diethylaminophenylmethane)
Figure 3C:
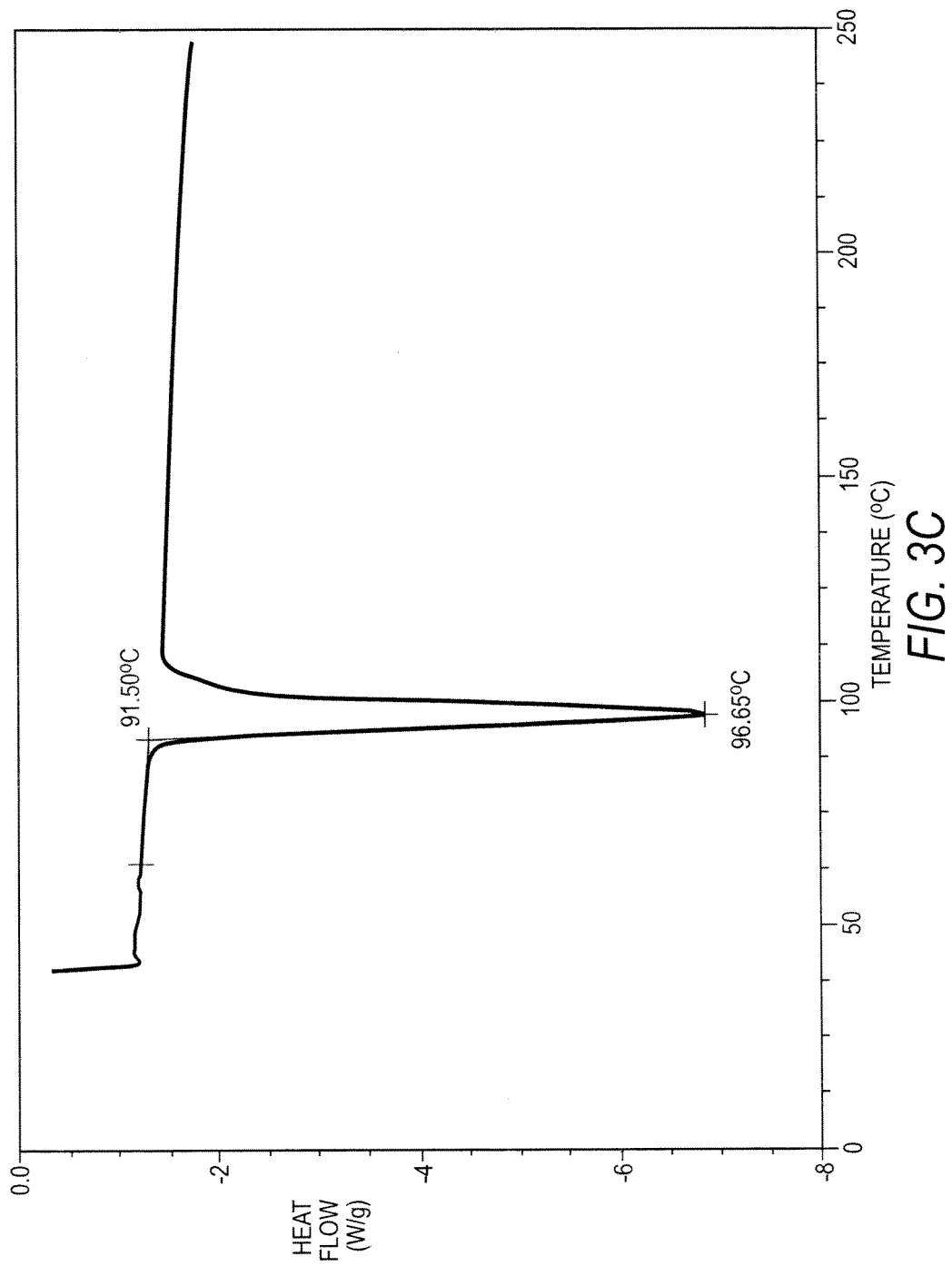
FIG. 3C is an evaluation made by DSC of the resulting product made by the processes for making bis(4-diethylamino-2-methylphenyl)-(4-diethylaminophenylmethane) according to the present embodiments.
Figure 3D:
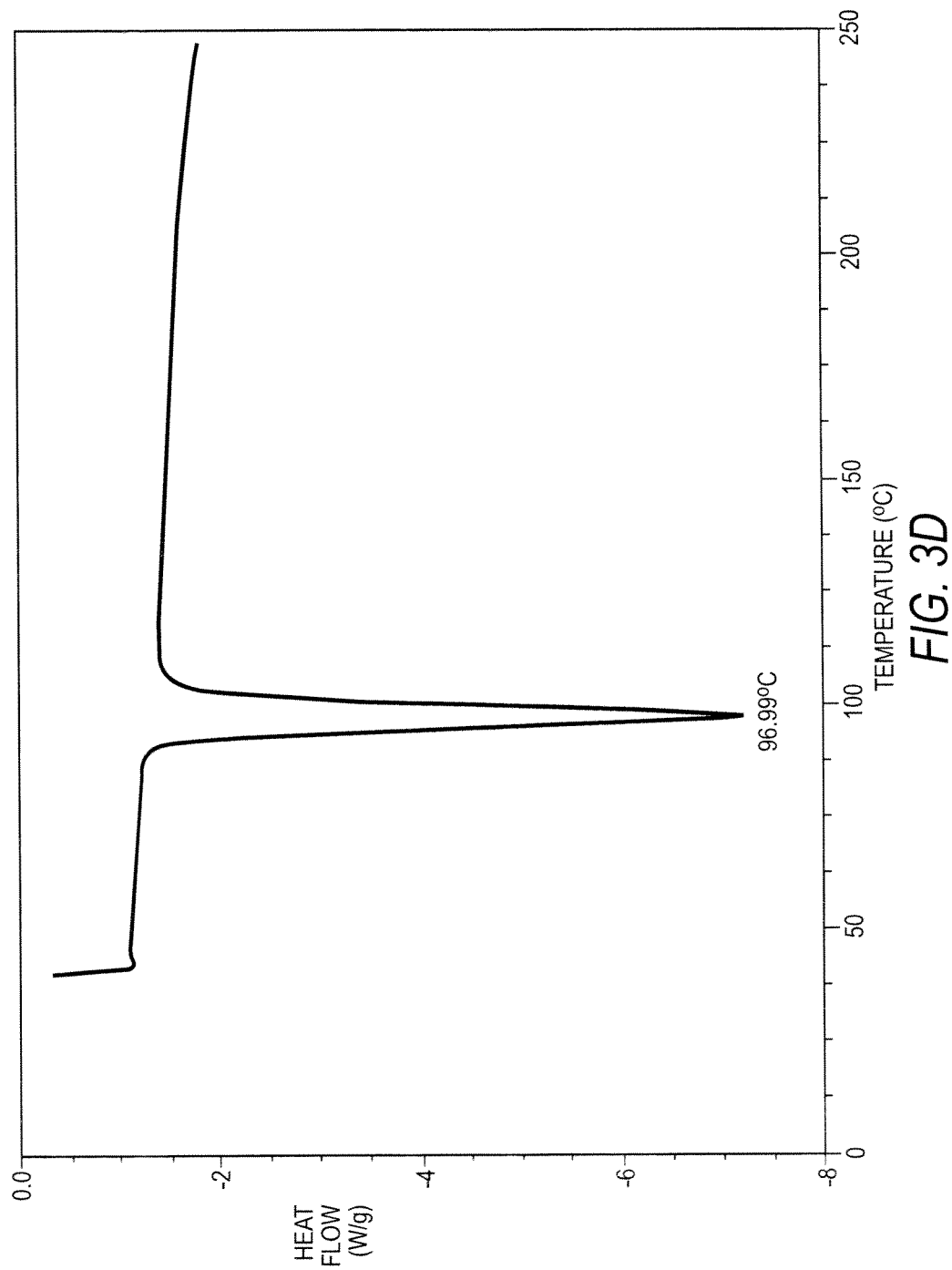
FIG. 3D is an evaluation made by DSC of another resulting product made by the processes for making bis(4-diethylamino-2-methylphenyl)-(4-diethylaminophenylmethane) according to the present embodiments.
Figure 4A:
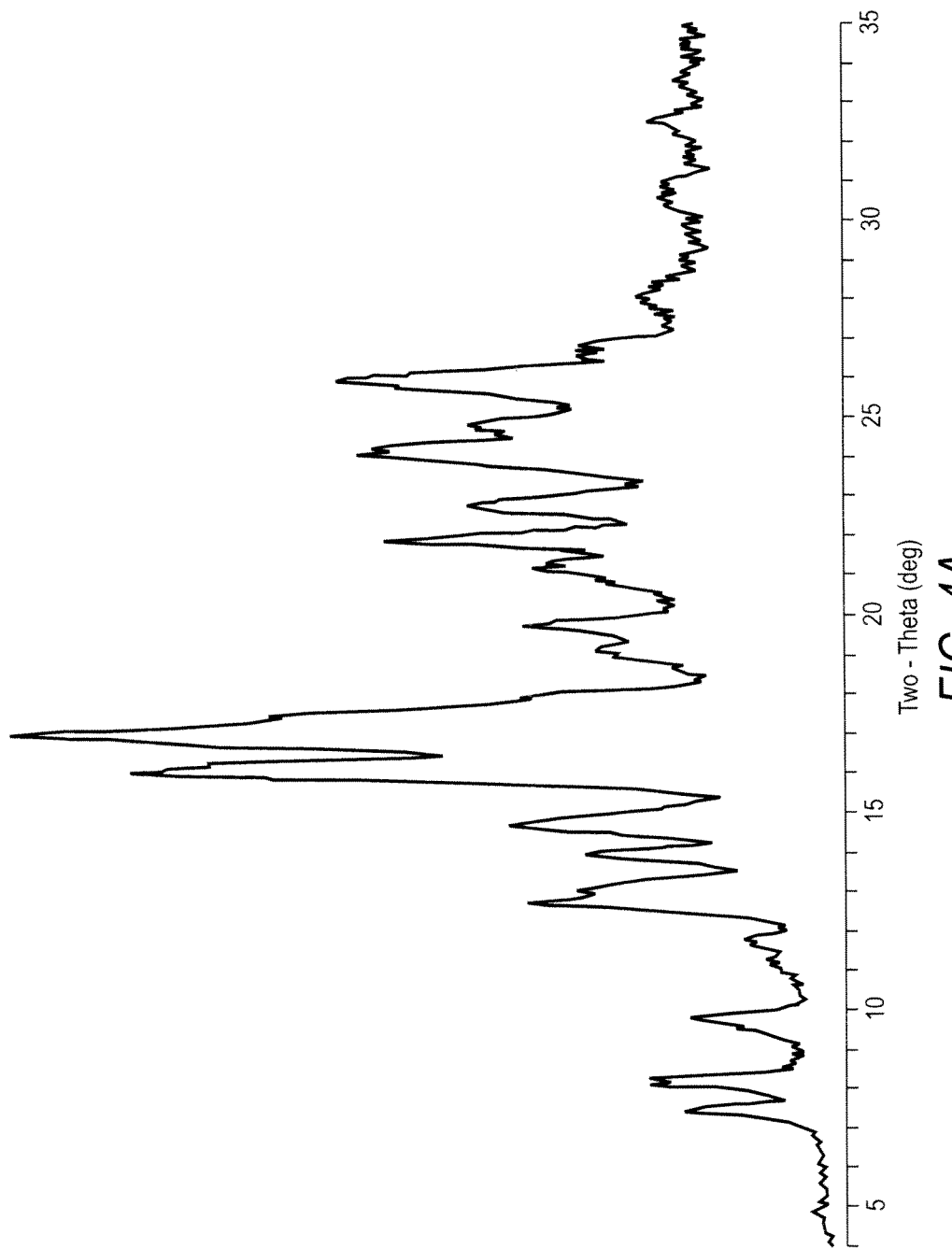
FIG. 4A is an evaluation made by x-ray diffraction (XRD) of the resulting product made by the conventional processes for making bis(4-diethylamino-2-methylphenyl)-(4-diethylaminophenylmethane)
Figure 4B:
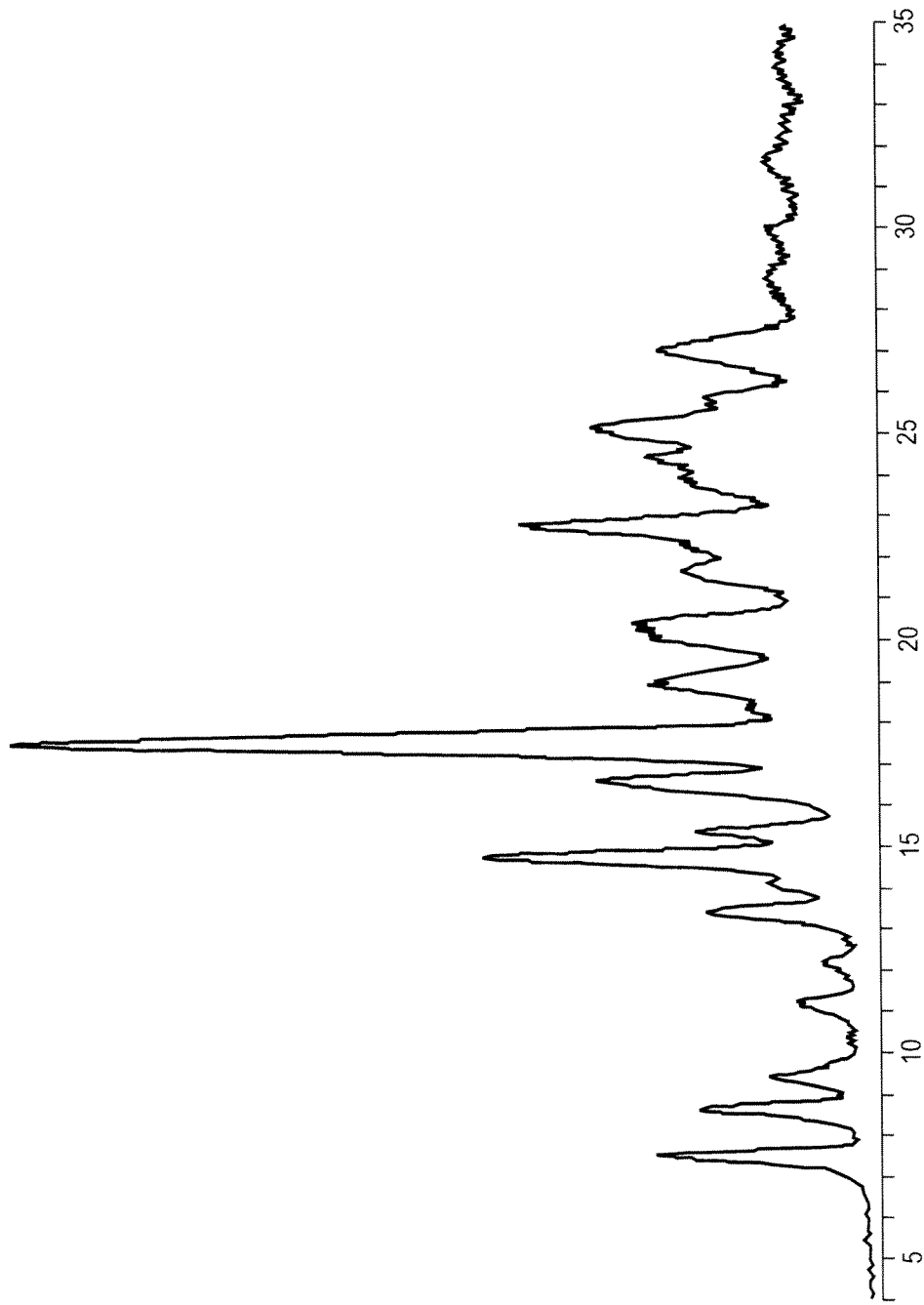
FIG. 4B is an evaluation made by x-ray diffraction (XRD) of another resulting product made by the conventional processes for making bis(4-diethylamino-2-methylphenyl)-(4-diethylaminophenylmethane)
Figure 4C:
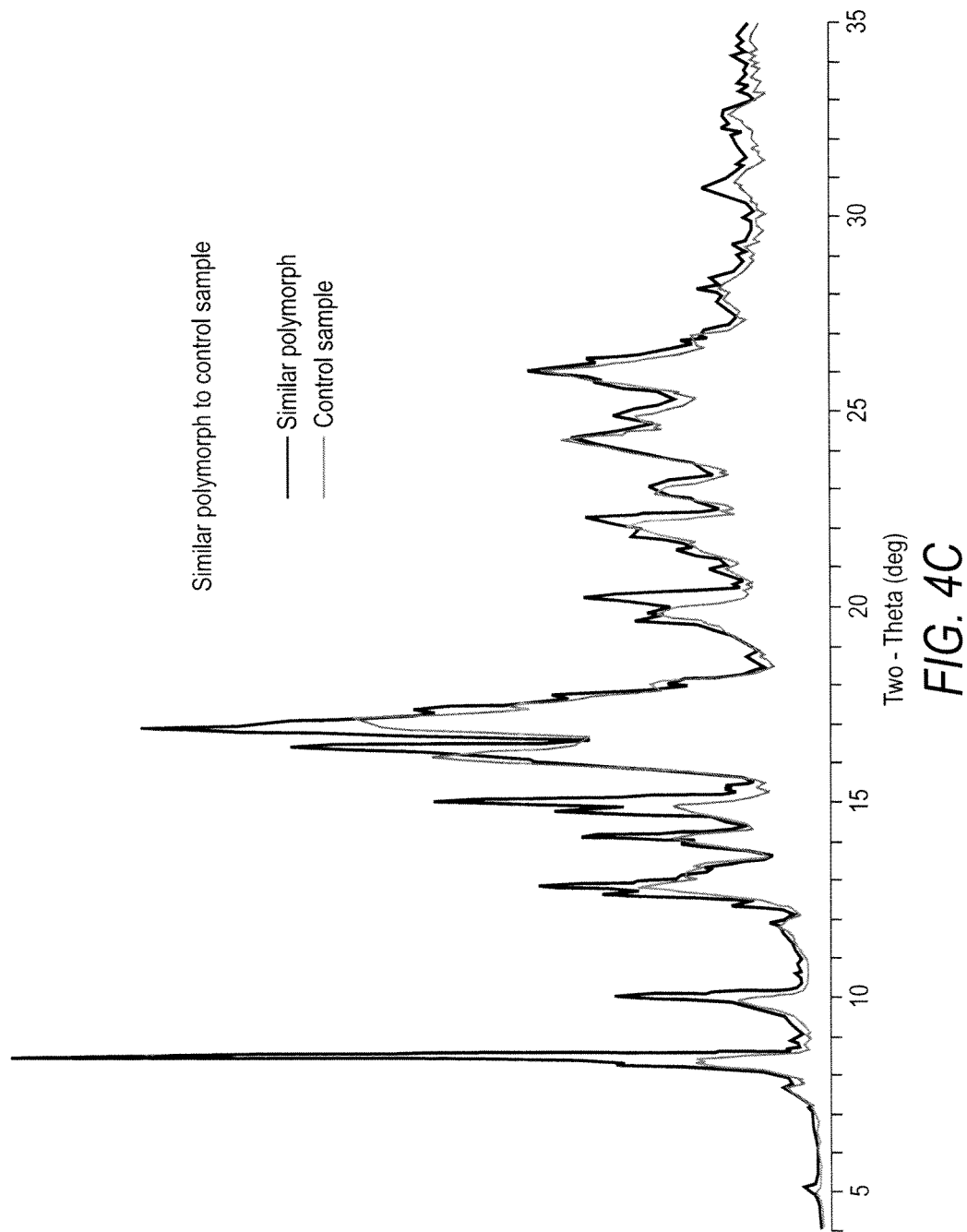
FIG. 4C is an evaluation made by XRD of the resulting product made by the processes for making bis(4-diethylamino-2-methylphenyl)-(4-diethylaminophenylmethane) according to the present embodiments.
Figure 4D:
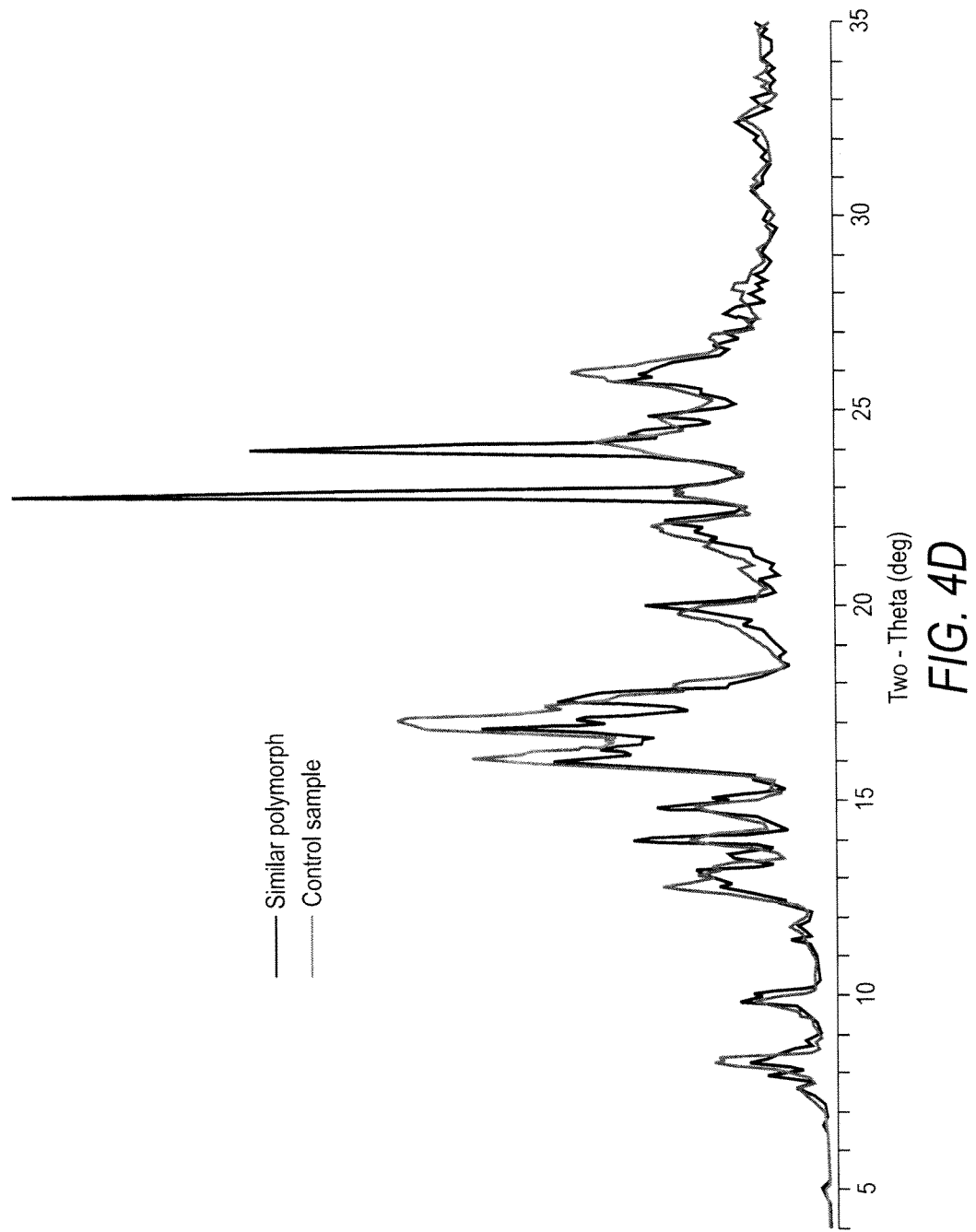
FIG. 4D is an evaluation made by XRD of another resulting product made by the processes for making bis(4-diethylamino-2-methylphenyl)-(4-diethylaminophenylmethane) according to the present embodiments.

As can be seen in FIGS. 3A and 3B, the differential scanning calorimetry (DSC) results show more consistency in the resulting product made from the process of the present embodiments (FIG. 3B) as compared to that made from the conventional process (FIG. 3A). In addition, FIGS. 4A and 4B shows evaluation of the compared products using x-ray diffraction (XRD). As can be seen, there is a higher degree of crystallinity produced in the Type A polymorph product made from the process of the present embodiments (FIG. 4B), as evidenced by the increase in number of peaks, as compared to that made from the conventional process (FIG. 4A).

In summary, there is provided a novel process for making bis(4-diethylamino-2-methylphenyl)-(4-diethylaminophenylmethane) which has many advantages over the prior used processes. In particular, the process of the present embodiments has been found to be repeatable, giving the same high purity results each time as well as faster and safer than the conventional processes.

All the patents and applications referred to herein are hereby specifically, and totally incorporated herein by reference in their entirety in the instant specification.

It will be appreciated that several of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, color, or material.

What is claimed is:

1. A process for making purified bis(4-diethylamino-2-methylphenyl)-(4-diethylaminophenylmethane) comprising:
dissolving crude bis(4-diethylamino-2-methylphenyl)-(4-diethylaminophenylmethane) in a first solvent room temperature to form dissolved crude bis(4-diethylamino-2-methylphenyl)-(4-diethylaminophenylmethane);
heating a mixture of a second solvent and a third solvent to a temperature of about 50° C. or higher to form a warm co-solvent mixture;
adding the dissolved crude bis(4-diethylamino-2-methylphenyl)-(4-diethylaminophenylmethane) to the warm co-solvent mixture in a drop-wise manner to form a precipitate mixture;
mixing the precipitate mixture;
cooling the precipitate mixture; and
drying the precipitate mixture to obtain the dried product comprising purified bis(4-diethylamino-2-methylphenyl)-(4-diethylaminophenylmethane), wherein the first, second and third solvents are not isopropanol.

2. The process of claim 1, wherein the first solvent is selected from the group consisting of methylethyl ketone, acetone, pentanone, cyclohexanone, and mixtures thereof.

3. The process of claim 1, wherein the second solvent is an alcohol.

4. The process of claim 1, wherein the third solvent is water.

5. The process of claim 1, wherein the first solvent is methyl ketone, the second solvent is ethanol and the third solvent is deionized water.

6. The process of claim 1, wherein the step of dissolving crude bis(4-diethylamino-2-methylphenyl)-(4-diethylaminophenylmethane) in the first solvent is performed at a temperature of from about 17 to about 28° C.

7. The process of claim 1, wherein the step of adding the dissolved crude bis(4-diethylamino-2-methylphenyl)-(4-diethylaminophenylmethane) to the warm co-solvent mixture is done at a rate of from about 5.0 g/min to about 130 g/min.

8. The process of claim 1, wherein the step of heating the co-solvent mixture is done in a jacketed reactor.

9. The process of claim 1, wherein the step of mixing the precipitate mixture is performed for from about 10 minutes to about 1 hour at a temperature of about 50° C. or higher.

10. The process of claim 9, wherein the step of mixing the precipitate mixture is performed for about 10 minutes at a temperature of about 50° C.

11. The process of claim 1, wherein a weight ratio of the amount of crude bis(4-diethylamino-2-methylphenyl)-(4-diethylaminophenylmethane) to the amount of the first solvent used is from about 1.4:1 to about 1:1.

12. The process of claim 1, wherein a ratio of the first solvent to the second solvent in the co-solvent mixture is from about 5:95 to about 95:5.

13. The process of claim 1, wherein a product recovery yield of the purified bis(4-diethylamino-2-methylphenyl)-(4-diethylaminophenylmethane) is about 85%.

14. The process of claim 1, wherein the drying step is performed by vacuum filtration.

15. A process for making purified bis(4-diethylamino-2-methylphenyl)-(4-diethylaminophenylmethane) comprising:
dissolving crude bis(4-diethylamino-2-methylphenyl)-(4-diethylaminophenylmethane) in a first solvent at room temperature to form dissolved crude bis(4-diethylamino-2-methylphenyl)-(4-diethylaminophenylmethane);
heating a mixture of a second solvent and a third solvent to a temperature of from about 50° to about 65° C. to form a warm co-solvent mixture;
adding the dissolved crude bis(4-diethylamino-2-methylphenyl)-(4-diethylaminophenylmethane) to the warm co-solvent mixture in a drop-wise manner to form a precipitate mixture;
mixing the precipitate mixture;
cooling the precipitate mixture; and
drying the precipitate mixture to obtain the dried product comprising purified bis(4-diethylamino-2-methylphenyl)-(4-diethylaminophenylmethane), wherein the purified bis(4-diethylamino-2-methylphenyl)-(4-diethylaminophenylmethane) is of Type A polymorph, wherein the first, second and third solvents are not isopropanol.

16. The process of claim 15, wherein the purified bis(4-diethylamino-2-methylphenyl)-(4-diethylaminophenylmethane) is a white powder.

17. A process for making an overcoat layer for an imaging member comprising:
- mixing together a melamine-formaldehyde crosslinking agent, a binder, a low surface energy compound, and an acid catalyst in a solvent to form an overcoat layer solution;
- adding an antioxidant comprising purified bis(4-diethylamino-2-methylphenyl)-(4-diethylaminophenylmethane) to the overcoat layer solution, the process of making the antioxidant comprising
- dissolving crude bis(4-diethylamino-2-methylphenyl)-(4-diethylaminophenylmethane) in a first solvent room temperature to form dissolved crude bis(4-diethylamino-2-methylphenyl)-(4-diethylaminophenylmethane),
- heating a mixture of a second solvent and a third solvent to a temperature of from about 50° to about 65° C. to form a warm co-solvent mixture,
- adding the dissolved crude bis(4-diethylamino-2-methylphenyl)-(4-diethylaminophenylmethane) to the warm co-solvent mixture in a drop-wise manner to form a precipitate mixture,
- mixing the precipitate mixture,
- cooling the precipitate mixture, and
- drying the precipitate mixture to obtain the dried product comprising purified bis(4-diethylamino-2-methylphenyl)-(4-diethylaminophenylmethane); and
- drying the overcoat layer solution to yield an overcoat layer, wherein the first, second and third solvents are not isopropanol.

18. The process of claim 17, wherein the overcoat layer has a thickness of from about 0.1 micrometer to about 10 micrometers.

19. The process of claim 17, wherein the purified bis(4-diethylamino-2-methylphenyl)-(4-diethylaminophenylmethane) is of Type A polymorph.

20. The process of claim 17, wherein the purified bis(4-diethylamino-2-methylphenyl)-(4-diethylaminophenylmethane) has a high degree of crystallinity.

* * * * *